United States Patent
Steinke et al.

(10) Patent No.: US 10,252,059 B2
(45) Date of Patent: Apr. 9, 2019

(54) METHOD AND APPARATUS FOR GUIDED OPTIMIZATION OF SPATIO-TEMPORAL PATTERNS OF NEUROSTIMULATION

(71) Applicant: Boston Scientific Neuromodulation Corporation, Valencia, CA (US)

(72) Inventors: G. Karl Steinke, Valencia, CA (US); Michael A. Moffitt, Saugus, CA (US); Hemant Bokil, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 43 days.

(21) Appl. No.: 15/394,409

(22) Filed: Dec. 29, 2016

(65) Prior Publication Data

US 2017/0189686 A1 Jul. 6, 2017

Related U.S. Application Data

(60) Provisional application No. 62/361,880, filed on Jul. 13, 2016, provisional application No. 62/273,062, filed on Dec. 30, 2015.

(51) Int. Cl.
*A61N 1/00* (2006.01)
*A61N 1/36* (2006.01)
(Continued)

(52) U.S. Cl.
CPC ....... *A61N 1/36146* (2013.01); *A61N 1/0551* (2013.01); *A61N 1/36062* (2017.08);
(Continued)

(58) Field of Classification Search
CPC .......... A61N 1/36146; A61N 1/36062
(Continued)

(56) References Cited

U.S. PATENT DOCUMENTS 6,516,227 B1 2/2003 Meadows et al.
7,321,797 B2 1/2008 Blamey et al.
(Continued)

FOREIGN PATENT DOCUMENTS

WO WO-2014117208 A1 8/2014
WO WO-2014159880 A1 10/2014
(Continued)

OTHER PUBLICATIONS

Dayan, Peter, et al., "Theoretical Neuroscience", Chapter 7 (MIT Press 2001) 54 pages.
(Continued)

*Primary Examiner* — Nadia A Mahmood
(74) *Attorney, Agent, or Firm* — Schwegman Lundberg & Woessner, P.A.

(57) ABSTRACT

An example of a system for programming a neurostimulator may include a storage device and a pattern generator. The storage device may store a pattern library and one or more neuronal network models. The pattern library may include fields and waveforms of neuromodulation. The one or more neuronal network models may each be configured to allow for evaluating effects of one or more fields in combination with one or more waveforms in treating one or more indications for neuromodulation. The one or more neuronal network models may include a first pain model configured to allow for optimization of neurostimulation using paresthesia, the second pain model configured to allow optimization of neurostimulation using anatomy. The pattern generator may be configured to construct and approximately optimize a spatio-temporal pattern of neurostimulation and/or its building blocks using at least one or more of the first pain model or the second pain model.

20 Claims, 12 Drawing Sheets

(51) Int. Cl.
*A61N 1/05* (2006.01)
*A61N 1/372* (2006.01)
*G06F 19/00* (2018.01)

(52) U.S. Cl.
CPC ..... *A61N 1/36071* (2013.01); *A61N 1/36128* (2013.01); *A61N 1/36135* (2013.01); *A61N 1/37247* (2013.01); *G06F 19/3481* (2013.01); *A61N 1/36132* (2013.01); *A61N 1/36139* (2013.01); *A61N 1/36185* (2013.01)

(58) Field of Classification Search
USPC .......................................................... 607/46
See application file for complete search history.

(56) References Cited

U.S. PATENT DOCUMENTS

| | | | |
|---|---|---|---|
| 7,783,353 | B2 | 8/2010 | Libbus et al. |
| 7,945,392 | B2 | 5/2011 | Siekmeier et al. |
| 8,285,389 | B2 | 10/2012 | Libbus et al. |
| 8,874,211 | B2 | 10/2014 | Libbus et al. |
| 8,923,981 | B2 | 12/2014 | Grill, Jr. et al. |
| 9,146,546 | B2 | 9/2015 | Sinyavskiy et al. |
| 9,265,948 | B2 | 2/2016 | Libbus et al. |
| 9,792,412 | B2 | 10/2017 | Moffitt et al. |
| 2005/0060010 | A1 | 3/2005 | Goetz |
| 2006/0095088 | A1 | 5/2006 | De Ridder |
| 2007/0203540 | A1 | 8/2007 | Goetz et al. |
| 2008/0004674 | A1 | 1/2008 | King et al. |
| 2014/0046397 | A1 | 2/2014 | Rohrer et al. |
| 2014/0081350 | A1 | 3/2014 | Zhu et al. |
| 2015/0134026 | A1 | 5/2015 | Kaula et al. |
| 2015/0134031 | A1 | 5/2015 | Moffitt et al. |
| 2016/0310739 | A1 | 10/2016 | Burdick et al. |
| 2017/0189685 | A1 | 7/2017 | Steinke et al. |
| 2017/0189687 | A1 | 7/2017 | Steinke et al. |
| 2017/0189688 | A1 | 7/2017 | Steinke et al. |
| 2017/0189689 | A1 | 7/2017 | Steinke et al. |

FOREIGN PATENT DOCUMENTS

| | | |
|---|---|---|
| WO | WO-2017117421 A1 | 7/2017 |
| WO | WO-2017117434 A1 | 7/2017 |
| WO | WO-2017117444 A1 | 7/2017 |
| WO | WO-2017117448 A1 | 7/2017 |
| WO | WO-2017117450 A1 | 7/2017 |

OTHER PUBLICATIONS

Gerstner, Wulfram, et al., "Spiking Neuron Models, Single Neurons, Populations, Plasticity", Chapter 4 (Cambridge University Press), 66 pages 2002.

Tass, P.A., "Desynchronization by Means of a Coordinated Reset of Neural Sub-Populations", Progress of Theoretical Physics Supplement, No. 150, 281-296 (2003).

Zhang, T.C., et al., "Modeling effects of spinal cord stimulation on wide-dynamic range dorsal horn neurons: influence of stimulation frequency and GABAergic inhibition", J Neurophysiol 112: 552-567, 2014.

"U.S. Appl. No. 15/394,379, Examiner Interview Summary dated Aug. 10, 2018", 3 pgs.

"U.S. Appl. No. 15/394,379, Final Office Action dated Jun. 19, 2018", 17 pgs.

"U.S. Appl. No. 15/394,379, Non Final Office Action dated Jan. 26, 2018", 17 pgs.

"U.S. Appl. No. 15/394,379, Notice of Allowance dated Sep. 25, 2018", 8 pgs.

"U.S. Appl. No. 15/394,379, Response filed Apr. 26, 2018 to Non Final Office Action dated Jan. 26, 2018", 13 pgs.

"U.S. Appl. No. 15/394,379, Response filed Aug. 20, 2018 to Final Office Action dated Jun. 19, 2018", 15 pgs.

"U.S. Appl. No. 15/394,439, Non Final Office Action dated Mar. 20, 2018", 10 pgs.

"U.S. Appl. No. 15/394,497, Final Office Action dated Jun. 15, 2018", 12 pgs.

"U.S. Appl. No. 15/394,497, Non Final Office Action dated Jan. 29, 2018", 15 pgs.

"U.S. Appl. No. 15/394,497, Notice of Allowance dated Sep. 11, 2018", 10 pgs.

"U.S. Appl. No. 15/394,497, Response filed Apr. 26, 2018 to Non Final Office Action dated Jan. 29, 2018", 30 pgs.

"U.S. Appl. No. 15/394,523, Restriction Requirement dated May 3, 2018", 6 pgs.

"Australian Application Serial No. 2016381015, First Examination Report dated Jul. 27, 2018", 3 pgs.

"International Application Serial No. PCT/US2016/069273, International Preliminary Report on Patentability dated Jul. 12, 2018", 8 pgs.

"International Application Serial No. PCT/US2016/069273, Search Report dated May 11, 2017", 4 pgs.

"International Application Serial No. PCT/US2016/069273, Written Opinion dated May 11, 2017", 6 pgs.

"International Application Serial No. PCT/US2016/069288, International Preliminary Report on Patentability dated Jul. 12, 2018", 8 pgs.

"International Application Serial No. PCT/US2016/069288, International Search Report dated Mar. 13, 2017", 5 pgs.

"International Application Serial No. PCT/US2016/069288, Written Opinion dated Mar. 13, 2017", 8 pgs.

"International Application Serial No. PCT/US2016/069300, International Preliminary Report on Patentability dated Jul. 12, 2018", 7 pgs.

"International Application Serial No. PCT/US2016/069300, International Search Report dated Apr. 28, 2017", 5 pgs.

"International Application Serial No. PCT/US2016/069300, Written Opinion dated Apr. 28, 2017", 5 pgs.

"International Application Serial No. PCT/US2016/069307, International Preliminary Report on Patentability dated Jul. 12, 2018", 7 pgs.

"International Application Serial No. PCT/US2016/069307, International Search Report dated Apr. 18, 2017", 5 pgs.

"International Application Serial No. PCT/US2016/069307, Written Opinion dated Apr. 18, 2017", 7 pgs.

"International Application Serial No. PCT/US2016/069312, International Preliminary Report on Patentability dated Jul. 12, 2018", 8 pgs.

"International Application Serial No. PCT/US2016/069312, International Search Report dated Apr. 13, 2017", 5 pgs.

"International Application Serial No. PCT/US2016/069312, Written Opinion dated Apr. 13, 2017", 6 pgs.

METHOD AND APPARATUS FOR GUIDED OPTIMIZATION OF SPATIO-TEMPORAL PATTERNS OF NEUROSTIMULATION

CLAIM OF PRIORITY

This application claims the benefit of priority under 35 U.S.C. § 119(e) of U.S. Provisional Patent Application Ser. No. 62/361,880, filed on Jul. 13, 2016 and U.S. Provisional Patent Application Ser. No. 62/273,062, filed on Dec. 30, 2015, which are incorporated by reference in their entirety.

CROSS REFERENCE TO RELATED APPLICATIONS

This application is related to commonly assigned U.S. Provisional Patent Application Ser. No. 62/361,847 entitled "METHOD AND APPARATUS FOR COMPOSING SPATIO-TEMPORAL PATTERNS OF NEUROSTIMULATION USING A NEURONAL NETWORK MODEL", filed on Jul. 13, 2016; U.S. Provisional Patent Application Ser. No. 62/361,862, entitled "METHOD AND APPARATUS FOR COMPOSING SPATIO-TEMPORAL PATTERNS OF NEUROSTIMULATION FOR CUMULATIVE EFFECTS", filed on Jul. 13, 2016; U.S. Provisional Patent Application Ser. No. 62/361,872, entitled "METHOD AND APPARATUS FOR OPTIMIZING SPATIO-TEMPORAL PATTERNS OF NEUROSTIMULATION FOR VARYING CONDITIONS", filed on Jul. 13, 2016; and U.S. Provisional Patent Application Ser. No. 62/361,886, entitled "METHOD AND APPARATUS FOR REDUCING SPATIAL SENSITIVITY IN NEUROSTIMULATION USING SPATIO-TEMPORAL FILTERING", filed on Jul. 13, 2016, which are incorporated by reference in their entirety.

TECHNICAL FIELD

This document relates generally to medical devices and more particularly to a system for neurostimulation programming including composition of stimulation patterns.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, the human nervous systems use neural signals having much more sophisticated patterns to communicate various types of information, including sensations of pain, pressure, temperature, etc. The nervous system may interpret an artificial stimulation with a simple pattern of stimuli as an unnatural phenomenon, and respond with an unintended and undesirable sensation and/or movement. For example, some neurostimulation therapies are known to cause paresthesia and/or vibration of non-targeted tissue or organ.

Recent research has shown that the efficacy and efficiency of certain neurostimulation therapies can be improved, and their side-effects can be reduced, by using patterns of neurostimulation pulses that emulate natural patterns of neural signals observed in the human body. While modern electronics can accommodate the need for generating such sophisticated pulse patterns, the capability of a neurostimulation system depends on its post-manufacturing programmability to a great extent. For example, a sophisticated pulse pattern may only benefit a patient when it is customized for that patient, and stimulation patterns predetermined at the time of manufacturing may substantially limit the potential for the customization. Such customization may be performed at least in part by a user such as a physician or other caregiver with the patient in a clinical setting.

SUMMARY

An example (e.g., "Example 1") of a system for programming a neurostimulator to deliver neurostimulation energy through a plurality of electrodes may include a storage device and a pattern generator. The storage device may be configured to store a pattern library and one or more neuronal network models. The pattern library may include a plurality of fields and a plurality of waveforms. The fields may each specify a spatial distribution of the neurostimulation energy across the plurality of electrodes. The waveforms may each specify a temporal pattern of the neuromodulation energy. The one or more neuronal network models may each be a computational model configured to allow for evaluating effects of one or more fields selected from the plurality of fields in combination with one or more waveforms selected from the plurality of waveforms in treating one or more indications for neuromodulation. The one or more neuronal network models may include at least one or more of a first pain model or a second pain model. The first pain model may be configured to allow for optimization of the spatio-temporal pattern of neurostimulation using paresthesia as a first guide. The second pain model may be configured to allow for optimization of the spatio-temporal pattern of neurostimulation using one or more locations of pain and one or more target regions to which neuromodulation is known to suppress the pain as a second guide. The pattern generator may be configured to generate a spatio-temporal pattern of neurostimulation specifying a sequence of one or more spatio-temporal units each including one or more fields selected from the plurality of fields in combination with one or more waveforms selected from the plurality of waveforms. The pattern generator may include a pattern editor and a pattern optimizer. The pattern editor may be configured to construct one or more of the plurality of fields, the plurality of waveforms, the one or more spatio-temporal units, or the spatio-temporal pattern of neurostimulation. The pattern optimizer may be configured to approximately optimize one or more of the plurality of fields, the plurality of waveforms, the one or more spatio-temporal units, or the spatio-temporal pattern of neurostimulation using at least one or more of the first pain model or the second pain model.

In Example 2, the subject matter of Example 1 may optionally be configured such that the one or more neuronal network models include the first pain model, and the pattern optimizer is configured to approximately optimize the spatio-temporal pattern of neurostimulation using the first pain model and one or more known paresthesia loci each being a set of fields of the plurality of fields identified for causing paresthesia.

In Example 3, the subject matter of Example 2 may optionally be configured such that the pattern optimizer is configured to approximately optimize the spatio-temporal pattern of neurostimulation using the first pain model and at least two known paresthesia loci.

In Example 4, the subject matter of any one or any combination of Examples 2 and 3 may optionally be configured such that the pattern optimizer is configured to approximately optimize the spatio-temporal pattern of neurostimulation by using the one or more known paresthesia loci as fields selected from the plurality of fields and approximately optimizing a waveform associated with each of the selected fields.

In Example 5, the subject matter of any one or any combination of Examples 2 to 4 may optionally be configured such that the pattern optimizer is configured to approximately optimize the spatio-temporal pattern of neurostimulation by using one or more regions surrounding the one or more known paresthesia loci as fields selected from the plurality of fields and approximately optimizing a waveform associated with each of the selected fields.

In Example 6, the subject matter of Example 5 may optionally be configured such that the pattern optimizer is configured to optimize one or more parameters of the waveform associated with each of the selected fields.

In Example 7, the subject matter of Example 5 may optionally be configured such that the pattern optimizer is configured to approximately optimize the spatio-temporal pattern of neurostimulation by using the one or more known paresthesia loci and one or more regions surrounding the one or more known paresthesia loci as fields selected from the plurality of fields and approximately optimizing a waveform associated with each of the selected fields.

In Example 8, the subject matter of any one or any combination of Examples 2 to 7 may optionally be configured such that the pattern optimizer is configured to approximately optimize the spatio-temporal pattern of neurostimulation using a plurality of different waveforms selected from the plurality of waveforms as the one or more waveforms specified in the spatio-temporal pattern of neurostimulation.

In Example 9, the subject matter of Example 8 may optionally be configured such that the pattern optimizer is configured to approximately optimize the spatio-temporal pattern of neurostimulation by including different spatio-temporal units of the one or more spatio-temporal units. The different spatio-temporal units target different regions of the patient's nervous system for delivering portions of the neurostimulation energy at times individually specified for each region of the different regions.

In Example 10, the subject matter of any one or any combination of Examples 2 to 9 may optionally be configured such that the pattern optimizer is configured to approximately optimize the spatio-temporal pattern of neurostimulation by using the first pain model and anatomy of regions of the one or more known paresthesia loci to identify additional one or more fields selected from the plurality of fields and approximately optimizing a waveform associated with each of the selected one or more additional fields.

In Example 11, the subject matter of Example 1 may optionally be configured such that the one or more neuronal network models include the second pain model, and the pattern optimizer is configured to select one or more fields selected from the plurality of fields for use in the spatio-temporal pattern of neurostimulation based on the one or more locations of pain and one or more target regions.

In Example 12, the subject matter of Example 11 may optionally be configured such that the pattern optimizer is configured to identify one or more field for use in the spatio-temporal pattern of neurostimulation based on the one or more locations of pain and one or more target regions and add the identified one or more fields to the plurality of fields if the identified one or more fields are not already included in the plurality of fields.

In Example 13, the subject matter of any one or any combination of Examples 11 and 12 may optionally be configured such that the pattern optimizer comprises a look-up table relating the one or more locations of pain to the one or more target regions, and identify the one or more target regions using a pain loci and the look-up table.

In Example 14, the subject matter of any one or any combination of Examples 11 to 13 may optionally be configured such that the pain model is further configured to allow optimization of the spatio-temporal pattern of neurostimulation using pain diagnosis as inputs.

In Example 15, the subject matter of any one or any combination of Examples 11 to 14 may optionally be configured such that the pattern optimizer is configured to generate a guide for placing the plurality of electrode in the patient based on the one or more fields specified in the spatio-temporal pattern of neurostimulation.

An Example (e.g., "Example 16") of a method for programming a neurostimulator is also provided. The method may include providing a pattern library, providing one or more neuronal network models, and generating a spatio-temporal pattern of neurostimulation. The pattern library may include a plurality of fields and a plurality of waveforms. The fields may each specify a spatial distribution of the neurostimulation energy across the plurality of electrodes. The waveforms may each specify a temporal pattern of the neuromodulation energy. The one or more neuronal network models may each be a computational model configured to allow for evaluating effects of one or more fields selected from the plurality of fields in combination with one or more waveforms selected from the plurality of waveforms in treating one or more indications for neuromodulation. The one or more neuronal network models may include at least one or more of a first pain model or a second pain model. The first pain model may be configured to allow for optimization of the spatio-temporal pattern of neurostimulation using paresthesia as a first guide. The second pain model may be configured to allow for optimization of the spatio-temporal pattern of neurostimulation using one or more locations of pain and one or more target regions to which neuromodulation is known to suppress the pain as a second guide. The spatio-temporal pattern of neurostimulation may specify a sequence of one or more spatio-temporal units each including one or more fields selected from the plurality of fields in combination with one or more waveforms selected from the plurality of waveforms. The generation of the spatio-temporal pattern of neurostimulation may include approximately optimizing one or more of the plurality of fields, the plurality of waveforms, the one or more spatio-temporal units, or the spatio-temporal pattern of neurostimulation using at least the one or more of the first pain model or the second pain model.

In Example 17, the subject matter of providing the one or more neuronal network models as found in Example 16 may optionally include providing the first pain model, and the subject matter of approximately optimizing the one or more of the plurality of fields, the plurality of waveforms, the one or more spatio-temporal units, or the spatio-temporal pattern of neurostimulation as found in Example 16 may optionally include approximately optimizing the spatio-temporal pattern of neurostimulation using the first pain model and one or more known paresthesia loci each being a set of fields of the plurality of fields identified for causing paresthesia.

In Example 18, the subject matter of approximately optimizing the spatio-temporal pattern of neurostimulation as found in Example 17 may optionally include approximately optimizing the spatio-temporal pattern of neurostimulation using a plurality of different waveforms selected from the plurality of waveforms as the one or more waveforms specified in the spatio-temporal pattern of neurostimulation.

In Example 19, the subject matter of providing the one or more neuronal network models as found in Example 16 may optionally include providing the second pain model, and the subject matter of approximately optimizing the one or more of the plurality of fields, the plurality of waveforms, the one or more spatio-temporal units, or the spatio-temporal pattern of neurostimulation as found in Example 16 may optionally include selecting one or more fields selected from the plurality of fields for use in the spatio-temporal pattern of neurostimulation based on the one or more locations of pain and one or more target regions.

In Example 20, the subject matter of any one or any combination of Examples 16 to 19 may optionally further include generating a guide for placing the plurality of electrode based on the one or more fields specified in the spatio-temporal pattern of neurostimulation.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
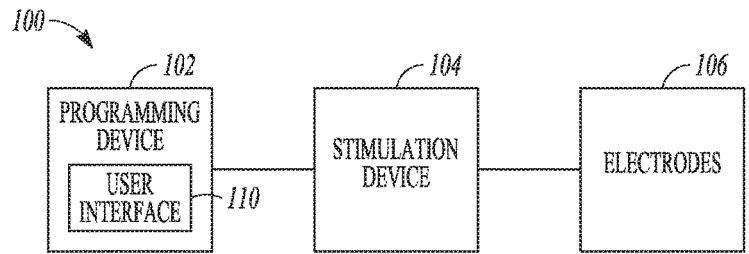
FIG. 1 illustrates an embodiment of a neurostimulation system.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a method and system for programming neurostimulation patterns. Advancements in neuroscience and neurostimulation research have led to a demand for using complex and/or individually optimized patterns of neurostimulation energy for various types of therapies. The capability of a neurostimulation system in treating various types of disorders will be limited by the programmability of such patterns of neurostimulation energy. In various embodiments, the present system allows for custom definition of a pattern of neurostimulation energy, which includes custom definition of waveforms being the building blocks of the pattern. In various embodiments, the present system may include a user interface that makes it possible for the user to perform the custom definition of potentially very complex patterns of neurostimulation pulses by creating and editing graphical representations of relatively simple individual building blocks for each of the patterns. In various embodiments, the individually definable waveforms may include, for example, pulses, bursts of pulses, trains of bursts, and sequences of pulses, bursts, and trains. In various embodiments, the present system may provide for patterns of neurostimulation energy not limited to waveforms predefined at the time of manufacturing, thereby accommodating need for customization of neurostimulation energy patterns as well as need for new types of neurostimulation energy patterns that may, for example, result from future research in neurostimulation. This may also facilitate design of a general-purpose neurostimulation device that can be configured by a user for delivering specific types of neurostimulation therapies by programming the device using the user interface.

In various embodiments, the present system (referred to as "the spatio-temporal system") includes a neurostimulator programming device with a user interface that enables users to understand, manage, and program stimulation and create patterns of stimuli specified by a complex combination of spatial and temporal parameters. Users of the programming device can have different levels of knowledge and expertise with respect to different aspects of programming a neurostimulator, as well as different needs and constraints. Examples include: a physician in an operation room may have very limited time for programming a neurostimulator for a patient under surgery; an academic researcher may have limited understanding of electrical engineering aspects of the stimulation; some users want to know what the stimuli look like, and some users may have limited understanding of anatomy, neuromodulation, and how electrical stimulation actually works. Therefore, the user interface provides access to different levels of access to various aspects of neurostimulation programming to reduce distraction, ensure accuracy and patient safety, and increase efficiency during programming of a neurostimulator. In one embodiment, multiple user interfaces, or multiple versions of a user interface, are configured for different stages of neurostimulation programming. For example, a user interface may be configured for composing waveforms, such as a spatio-temporal pattern of neurostimulation and its building blocks, as discussed in this document. Another user interface may be configured for sharing the composed waveforms with other users. Still another user interface may be configured for programming a stimulator for each individual patient. Yet another user interface may be configured for use by the user and/or the patient to adjust the programming as needed when one or more neurostimulation therapies are delivered to the patient. User interface(s) may be configured to provide any combination of two or more of these functions.

In various embodiments, the user interface allows for neurostimulation programming starting with templates/presets to enable valuable time savings in defining stimulation waveforms. In various embodiments, the user interface provides for complete editorial control as well as simplified, guided, and template-based editorial options. In various embodiments, the user interface provides the user with interpretation of editorial features and guide rails.

In various embodiments, the present system may be implemented using a combination of hardware and software designed to provide users such as researchers, physicians or other caregivers, or neurostimulation device makers with ability to create custom waveforms and patterns in an effort to increase therapeutic efficacy, increase patient satisfaction for neurostimulation therapies, reduce side effects, and/or increase device longevity. The present system may be applied in any neurostimulation (neuromodulation) therapies, including but not being limited to SCS, DBS, PNS, FES, and Vagus Nerve Stimulation (VNS) therapies.

The present system is highly flexible in its ability to generate non-uniform patterns of neurostimulation energy as well as shapes of waveform building blocks other than "standard" shapes (e.g., square and exponential pulses). It expands temporal programming capability of known neurostimulation programming systems. The present system has strong capabilities in both space (which neural elements are modulated) and time (what information is conveyed to those neural elements) that are potentially potent combination for achieving neurostimulation objectives when interacting with complex neural systems. The present system can "talk" to different groups of neural elements and/or their support elements and "tell" them the "right" information to obtain a desired clinical effect.

Neuronal models have been built (e.g., by various academic groups) to indicate that engaging multiple groups of neurons that are part of a network of interest can be exploited to achieve a desired output. These groups of neurons can often be separated by certain characteristics, such as fiber diameter, primary output neurotransmitter, and spatial/anatomical location. The present subject matter uses such neuronal models in the programming of neurostimulation including composition of patterns of neurostimulation. Use of neuronal models may, for example, allow a substantial part of customization of a pattern of neurostimulation for a patient to be performed without the presence of patient. Use of neuronal models may also, for example, allow researchers to evaluating various new patterns of neurostimulation and their building blocks using computer simulations.

The present subject matter provides methods for selecting electric field loci that correspond to the groups of neural elements of interest. One embodiment uses paresthesia-based methods to guide selection of field loci (see discussion under "F. Paresthesia-Guided Field Selection" below). One embodiment uses anatomical-based methods (see discussion under "G. Anatomy-Guided Field Selection" below). One embodiment uses a filter with less spatial sensitivity (see discussion under "H. Spatio-Temporal Filtering to Reduce Spatial Sensitivity" below).

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered, including relative timing between pulses delivered through different sets of electrodes. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100 as well as researchers or other professional developing such treatments; a "patient" includes a person who receives or is intended to receive neurostimulation delivered using system 100. In various embodiments, the patient nay be allowed to adjust his or her treatment using system 100 to certain extent, such as by adjusting certain therapy parameters and entering feedback and clinical effects information. While neurostimulation energy delivered in the form of electrical pulses is discussed in various portions of this document as a specific example of stimuli of the neurostimulation, various embodiments may use any type of neurostimulation energy delivered in any type of stimuli that are capable of modulating characteristics and/or activities in neural or other target tissue in a patient. When electrical energy is used for neurostimulation, stimuli may include pulses with various shapes and phases, as well as continuous signals such as signals with sinusoidal waveforms.

In various embodiments, programming device 102 includes a user interface that allows the user to set and/or adjust values of the user-programmable parameters by creating and/or editing graphical representations of various waveforms. Such waveforms may include, for example, the waveform of a pattern of neurostimulation pulses to be delivered to the patient as well as waveform building blocks that can be used in the pattern of neurostimulation pulses. Examples of such waveform building blocks include pulses, bursts each including a group of the pulses, trains each including a group of the bursts, and sequences each including a group of the pulses, bursts, and trains, as further discussed below. In various embodiments, programming device 102 allows the user to edit existing waveform building blocks, create new waveform building blocks, import waveform building blocks created by other users, and/or export waveform building blocks to be used by other users. The user may also be allowed to define an electrode selection specific to each individually defined waveform. In the illustrated embodiment, the user interface includes a user interface 110. In various embodiments, user interface 110 may include a GUI or any other type of user interface accommodating various functions including waveform composition as discussed in this document.

Figure 2:
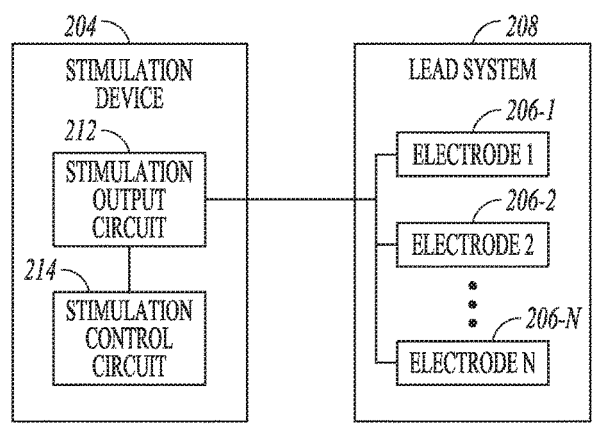
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads with 8 electrodes incorporated onto each lead. In various embodiments, stimulation output circuit 212 may support X total electrodes (or contacts, such as electrodes selected from electrodes 206) in a system such as system 100, of which Y electrodes may be activated for a therapy session, of which Z electrodes (Z<Y) may be activated simultaneously during the therapy session. The system may have W electrical sources for delivering the neurostimulation pulses, where W is greater than Y but may be smaller than X. For example, stimulation output circuit 212 may have W timing channels, where W is greater than Y but may be smaller than X.

Figure 3:
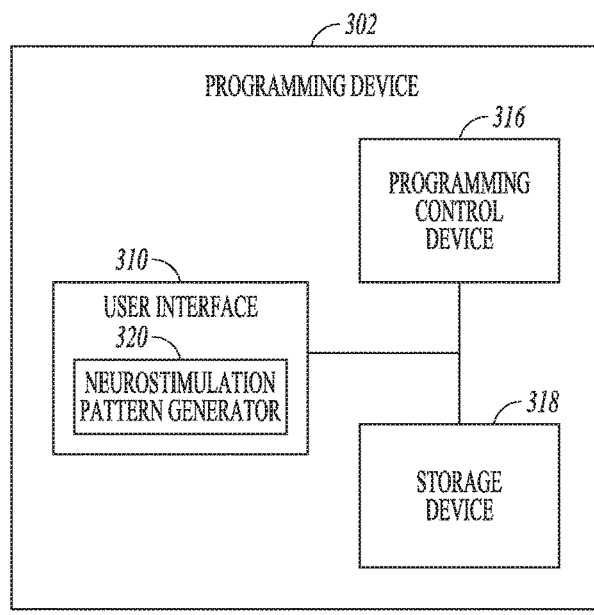
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Storage device 318 stores a plurality of waveform building blocks. Programming control circuit 316 generates the plurality of stimulation parameters that controls the delivery of the neurostimulation pulses according to the pattern of the neurostimulation pulses. User interface 310 represents an embodiment of GUI 110 and allows the user to define the pattern of the neurostimulation pulses using one or more waveform building blocks selected from the plurality of waveform building blocks.

In various embodiments, user interface 310 includes a neurostimulation pattern generator 320 that allows the user to manage the waveform building blocks, including importing waveform building blocks to be added to the waveform building blocks stored in storage device 318, exporting waveform building blocks selected from the waveform building blocks stored in storage device 318, and editing each of the waveform building blocks. In various embodiments, user interface 310 includes a GUI that allows for graphical editing of each of the waveform building blocks. In various embodiments, neurostimulation pattern generator 320 allows the user to create the pattern of neurostimulation pulses to be delivering to the patient using stimulation device 104 using waveform building blocks such as pulses, bursts each including a group of the pulses, trains each including a group of the bursts, and/or sequences each including a group of the pulses, bursts, and trains. In various embodiments, neurostimulation pattern generator 320 allows the user to create each waveform building block using one or more waveform building blocks stored in storage device 318 as templates. In various embodiments, neurostimulation pattern generator 320 allows each newly created waveform building block to be saved as additional waveform building block stored in storage device 318.

In one embodiment, user interface 310 includes a touchscreen. In various embodiments, user interface 310 includes any type of presentation device, such as interactive or non-interactive screens, and any type of user input devices that allow the user to edit the waveforms or building blocks and schedule the programs, such as touchscreen, keyboard, keypad, touchpad, trackball, joystick, mouse, virtual reality (VR) control, multi-touch, voice control, inertia/accelerometer-based control, and vision-based control. In various embodiments, circuits of neurostimulation 100, including its various embodiments discussed in this document, may be implemented using a combination of hardware and software. For example, the circuit of user interface 100, stimulation control circuit 214, and programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
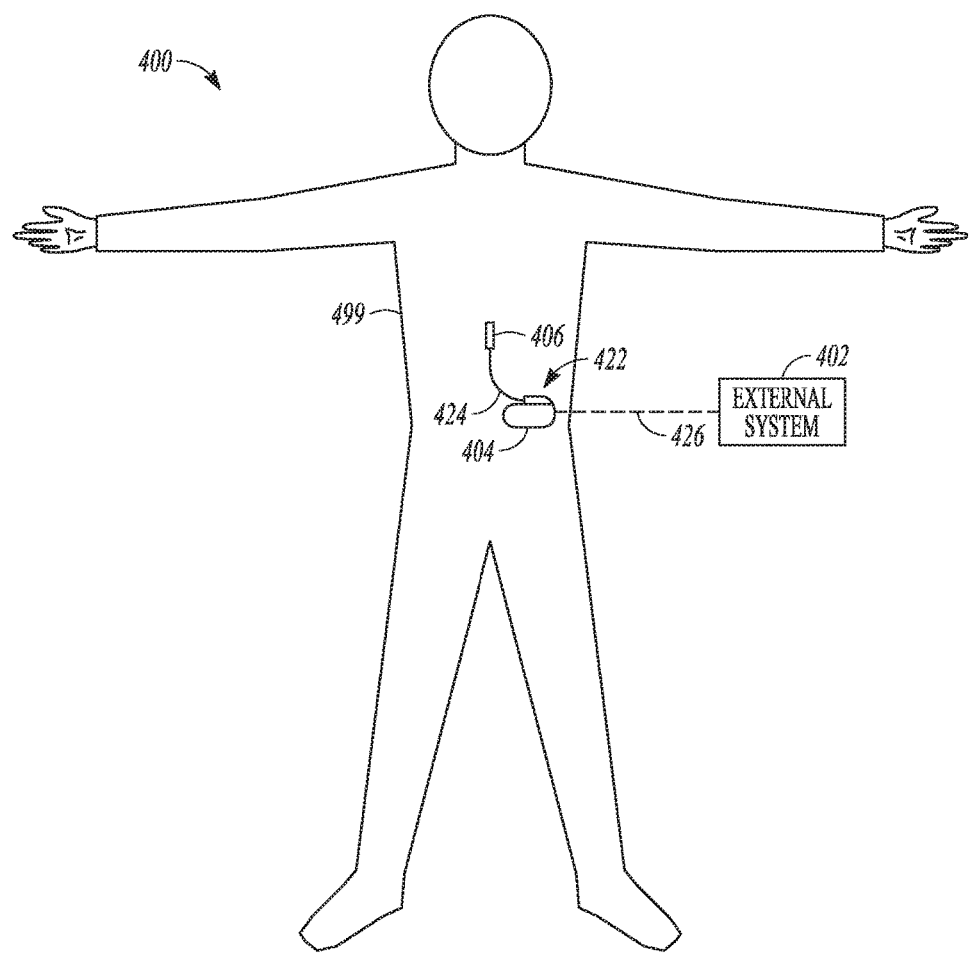
FIG. 4 illustrates an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between implantable system 422 and external system 402. Implantable system 422 is illustrated in FIG. 4 as being implanted in the patient's body 499.

Implantable system 422 includes an implantable stimulator (also referred to as an implantable pulse generator, or IPG) 404, a lead system 424, and electrodes 406, which represent an embodiment of stimulation device 204, lead system 208, and electrodes 206, respectively. External system 402 represents an embodiment of programming device 302. In various embodiments, external system 402 includes one or more external (non-implantable) devices each allowing the user and/or the patient to communicate with implantable system 422. In some embodiments, external 402 includes a programming device intended for the user to initialize and adjust settings for implantable stimulator 404 and a remote control device intended for use by the patient. For example, the remote control device may allow the patient to turn implantable stimulator 404 on and off and/or adjust certain patient-programmable parameters of the plurality of stimulation parameters.

The sizes and shapes of the elements of implantable system 422 and their location in body 499 are illustrated by way of example and not by way of restriction. An implantable system is discussed as a specific application of the programming according to various embodiments of the present subject matter. In various embodiments, the present subject matter may be applied in programming any type of stimulation device that uses electrical pulses as stimuli, regardless of stimulation targets in the patient's body and whether the stimulation device is implantable.

Figure 5:
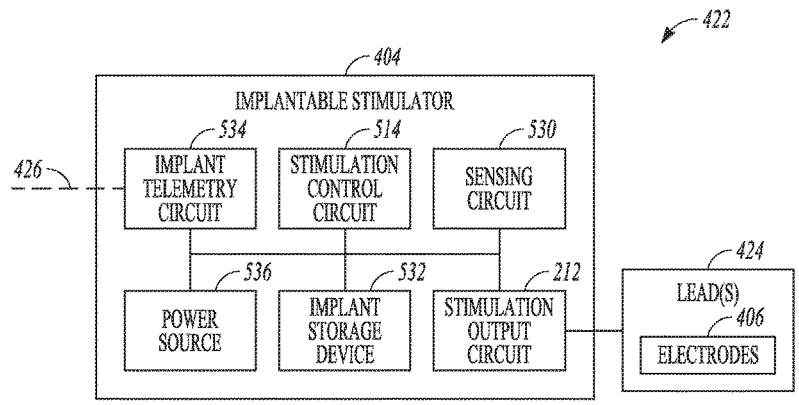
FIG. 5 illustrates an embodiment of an implantable stimulator and one or more leads of an implantable neurostimulation system, such as the implantable system of FIG. 4.

FIG. 5 illustrates an embodiment of implantable stimulator 404 and one or more leads 424 of an implantable neurostimulation system, such as implantable system 422. Implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. Sensing circuit 530, when included and needed, senses one or more physiological signals for purposes of patient monitoring and/or control of the neurostimulation. Examples of the one or more physiological signals includes neural and other signals each indicative of a condition of the patient that is treated by the neurostimulation and/or a response of the patient to the delivery of the neurostimulation. In various embodiments, additional signals may be generated by processing the sensed one or more physiological signals, such as by correlation, subtraction, and/or being used as inputs to conditional, rules based state machines, for purposes of patient monitoring and/or control of the neurostimulation. Stimulation output circuit 212 is electrically connected to electrodes 406 through lead 424, and delivers each of the neurostimulation pulses through a set of electrodes selected from electrodes 406. Stimulation control circuit 514 represents an embodiment of stimulation control circuit 214 and controls the delivery of the neurostimulation pulses using the plurality of stimulation parameters specifying the pattern of the neurostimulation pulses. In one embodiment, stimulation control circuit 514 controls the delivery of the neurostimulation pulses using the one or more sensed physiological signals. Implant telemetry circuit 534 provides implantable stimulator 404 with wireless communication with another device such as a device of external system 402, including receiving values of the plurality of stimulation parameters from external system 402. Implant storage device 532 stores values of the plurality of stimulation parameters. Power source 536 provides implantable stimulator 404 with energy for its operation. In one embodiment, power source 536 includes a battery. In one embodiment, power source 536 includes a rechargeable battery and a battery charging circuit for charging the rechargeable battery. Implant telemetry circuit 534 may also function as a power receiver that receives power transmitted from external system 402 through an inductive couple or another mechanism.

In various embodiments, sensing circuit 530 (if included), stimulation output circuit 212, stimulation control circuit 514, implant telemetry circuit 534, implant storage device 532, and power source 536 are encapsulated in a hermetically sealed implantable housing. In various embodiments, lead(s) 424 are implanted such that electrodes 406 are placed on and/or around one or more targets to which the neurostimulation pulses are to be delivered, while implantable stimulator 404 is subcutaneously implanted and connected to lead(s) 424 at the time of implantation.

Figure 6:
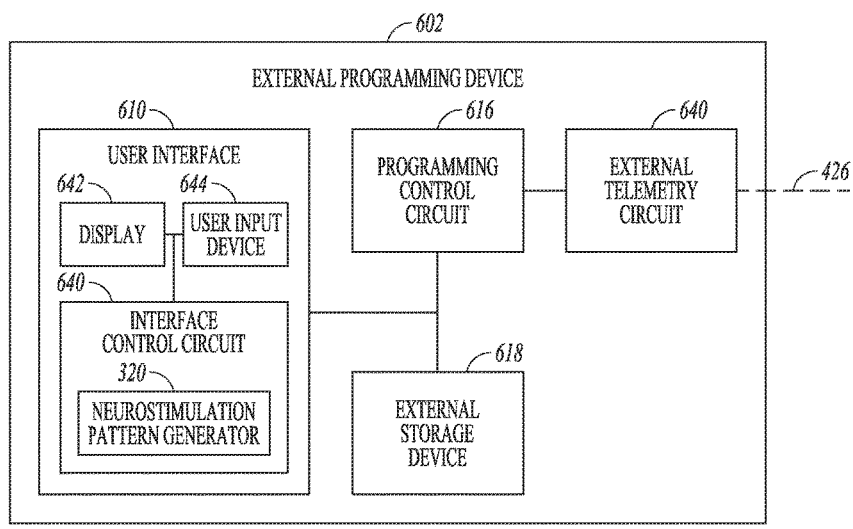
FIG. 6 illustrates an embodiment of an external programming device of an implantable neurostimulation system, such as the external system of FIG. 4.

FIG. 6 illustrates an embodiment of an external programming device 602 of an implantable neurostimulation system, such as external system 402. External programming device 602 represents an embodiment of programming device 302, and includes an external telemetry circuit 646, an external storage device 618, a programming control circuit 616, and a user interface 610.

External telemetry circuit 646 provides external programming device 602 with wireless communication with another device such as implantable stimulator 404 via telemetry link 426, including transmitting the plurality of stimulation parameters to implantable stimulator 404. In one embodiment, external telemetry circuit 646 also transmits power to implantable stimulator 404 through the inductive couple.

External storage device 618 stores a plurality of waveform building blocks each selectable for use as a portion of the pattern of the neurostimulation pulses. In various embodiments, each waveform building block of the plurality of waveform building blocks includes one or more pulses of the neurostimulation pulses, and may include one or more other waveform building blocks of the plurality of waveform building blocks. Examples of such waveforms include pulses, bursts each including a group of the pulses, trains each including a group of the bursts, and sequences each including a group of the pulses, bursts, and trains. External storage device 618 also stores a plurality of stimulation fields. Each waveform building block of the plurality of waveform building blocks is associated with one or more fields of the plurality of stimulation fields. Each field of the plurality of stimulation fields is defined by one or more electrodes of the plurality of electrodes through which a pulse of the neurostimulation pulses is delivered and a current distribution of the pulse over the one or more electrodes.

Programming control circuit 616 represents an embodiment of programming control circuit 316 and generates the plurality of stimulation parameters, which is to be transmitted to implantable stimulator 404, according to the pattern of the neurostimulation pulses. The pattern is defined using one or more waveform building blocks selected from the plurality of waveform building blocks stored in external storage device 618. In various embodiment, programming control circuit 616 checks values of the plurality of stimulation parameters against safety rules to limit these values within constraints of the safety rules. In one embodiment, the safety rules are heuristic rules. In various embodiments, it may be a requirement that the plurality of stimulation parameters is experienced by the patient or subject before the programming is complete (e.g., for use during a therapy session). This may include, for example, that the patient or subject experiences the whole set of the parameters, a representative subset of the parameters, or a representative set of the parameters defined via processing, to ensure suitability and tolerance of the expected stimulation that will be experienced by the patient during a therapy session.

User interface 610 represents an embodiment of user interface 310 and allows the user to define the pattern of neurostimulation pulses and perform various other monitoring and programming tasks. In one embodiment, user interface 610 includes a GUI. User interface 610 includes a display 642, a user input device 644, and an interface control circuit 640. Display 642 may include any type of visual display such as interactive or non-interactive screens, and user input device 644 may include any type of user input devices that supports the various functions discussed in this document, such as touchscreen, keyboard, keypad, touchpad, trackball, joystick, and mouse. In one embodiment, user interface 610 includes a GUI that has an interactive screen for displaying a graphical representation of a waveform building block and allows the user to adjust the waveform building block by graphically editing the waveform building block. Actions of the graphical editing may be scripted, or otherwise automated, or performed programmatically. In one embodiment, "graphically editing" may include keyboard actions, such as actions sometimes referred to as "keyboard shortcuts". User interface 610 may also allow the user to perform any other functions discussed in this document where graphical editing is suitable as may be appreciated by those skilled in the art.

Interface control circuit 640 controls the operation of user interface 610 including responding to various inputs received by user input device 644 and defining the one or more stimulation waveforms. Interface control circuit 640 includes neurostimulation pattern generator 320.

In various embodiments, external programming device 602 has operation modes including a composition mode and a real-time programming mode. In other embodiments, such operation modes may exist as separate software suites, interfaces to remote applications (such as "web-apps"), or be located on one or more physical devices other than external programming device 602. Under the composition mode (also known as the pulse pattern composition mode), User interface 610 is activated, while programming control circuit 616 is inactivated. Programming control circuit 616 does not dynamically updates values of the plurality of stimulation parameters in response to any change in the one or more stimulation waveforms. Under the real-time programming mode, both user interface 610 and programming control circuit 616 are activated. Programming control circuit 616 dynamically updates values of the plurality of stimulation parameters in response to changes in the set of one or more stimulation waveforms, and transmits the plurality of stimulation parameters with the updated values to implantable stimulator 404. In various embodiments, the transmission of the plurality of stimulation parameters to implantable stimulator 404 may be gated by a set of rules. Implantable stimulator 404 may be instructed to operate one set of parameters that is a processed version of the dynamically updated set of parameters until programming is closed. For example, a burst A may be delivered followed by a pause B and then followed by another burst C, where pause B is long. Implantable stimulator 404 may replace the long pause B with a short pause D when the programmer and/or system identifies that long pause B does not affect the patient's experience of either burst A or C.

A. Neurostimulation Programming Using Neuronal Network Model

Figure 7:
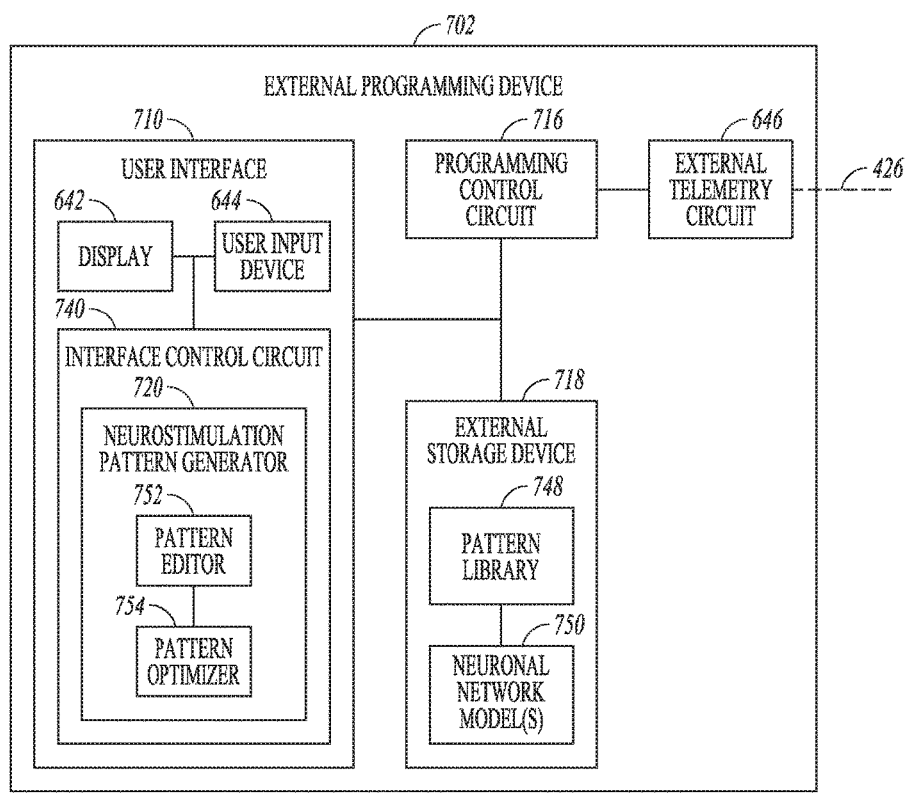
FIG. 7 illustrates another embodiment of the external programming device of FIG. 6.

FIG. 7 illustrates an embodiment of an external programming device 702, which represents an embodiment of external programming device 602. External programming device 702 includes external telemetry circuit 646, an external storage device 718, a programming control circuit 716, and a user interface 710. In various embodiments, external programming device 702 may be implemented as a single device or multiple devices communicatively coupled to each other.

External storage device 718 represents an embodiment of external storage device 618 and may store a pattern library (database) 748 and one or more neuronal network models 750. Pattern library 748 may include a plurality of fields (spatial patterns) and a plurality of waveforms (temporal patterns). Each field of the plurality of fields specifies a spatial distribution of the neurostimulation energy across a plurality of electrodes such as electrodes 406. In various embodiments, the spatial distribution can be specified by an amplitude of the energy for each electrode or a fraction of the total energy for each electrode. When the spatial distribution is specified by a percentage of the total energy for each electrode, for example, 0% assigned to an electrode means that electrode is not actively used, and 100% assigned to an electrode means that electrode is the only electrode actively used, such as during a particular phase of the neurostimulation. Each waveform of the plurality of waveforms specifies a waveform of a sequence of the neuromodulation pulses. Certain parameters, such as amplitude of neurostimulation pulses (e.g., in mA), may be defined in either the fields or the waveforms. One or more neuronal network models 750 are each a computational model configured to allow for evaluating effects of one or more fields selected from the plurality of fields in combination with one or more waveforms selected from the plurality of waveforms in treating one or more indications for neurostimulation. In various embodiments, the effects include one or more therapeutic effects in treating one or more indications for neuromodulation. In various embodiments, the effects include one or more therapeutic effects in treating one or more indications for neuromodulation and one or more side effects associated with the neuromodulation. In various embodiments, external storage device 718 may include one or more storage devices. Programming control circuit 716 represents an embodiment of programming control circuit 616 and generates a plurality of stimulation parameters controlling delivery of neurostimulation pulses from a neurostimulator, such as implantable stimulator 404, according to a spatio-temporal pattern of neurostimulation. The spatio-temporal pattern of neurostimulation specifies a sequence of neurostimulation pulses grouped as one or more spatio-temporal units. The one or more spatio-temporal units each include one or more fields selected from the plurality of fields in combination with one or more waveforms selected from the plurality of waveforms.

User interface 710 represents an embodiment of user interface 610 and includes display 642, user input device 644, and an interface control circuit 740. Interface control circuit 740 represents an embodiment of interface control circuit 640 and includes a neurostimulation pattern generator 720 that generates the spatio-temporal pattern of neurostimulation. Neurostimulation pattern generator 720 represents an embodiment of neurostimulation pattern generator 320 and includes a pattern editor 752 and a pattern optimizer 754. Pattern editor 752 allows the user to create and adjust one or more of the plurality of fields, the plurality of waveforms, the one or more spatio-temporal units, or the spatio-temporal pattern of neurostimulation. Examples of pattern editor 752 are discussed in U.S. patent application Ser. No. 14/853,589, entitled "GRAPHICAL USER INTERFACE FOR PROGRAMMING NEUROSTIMULATION PULSE PATTERNS", filed on Sep. 14, 2015; U.S. patent application Ser. No. 14/926,725, entitled "METHOD AND APPARATUS FOR PROGRAMMING COMPLEX NEUROSTIMULATION PATTERNS", filed on Oct. 29, 2015; U.S. Provisional Patent Application Ser. No. 62/137,567, entitled "METHOD AND APPARATUS FOR CONTROLLING TEMPORAL PATTERNS OF NEUROSTIMULATION", filed on Mar. 24, 2015; U.S. Provisional Patent Application Ser. No. 62/111,715, entitled "METHOD AND APPARATUS FOR PROGRAMMING CHARGE RECOVERY IN NEUROSTIMULATION WAVEFORM", filed on Feb. 4, 2015; U.S. Provisional Patent Application Ser. No. 62/198,957, entitled "USER INTERFACE FOR CUSTOM PATTERNED ELECTRICAL STIMULATION", filed on Jul. 30, 2015; and U.S. Provisional Patent Application Ser. No. 62/241,965, entitled "USER INTERFACE FOR NEUROSTIMULATION WAVEFORM COMPOSITION", filed on Oct. 15, 2015, all assigned to Boston Scientific Neuromodulation Corporation, which are incorporated herein by reference in their entirety. Pattern optimizer 754 approximately optimizes one or more of the plurality of fields, the plurality of waveforms, the one or more spatio-temporal units, or the spatio-temporal pattern of neurostimulation using at least one neuronal network model of one or more neuronal models 750.

In various embodiments in which external programming device 702 is implemented as multiple devices communicatively coupled to each other, one or more of the multiple devices may each include a user interface similar to user interface 710. In various embodiments, external programming device 702 includes an additional pattern optimizer that can be communicatively coupled to pattern optimizer 754. In one embodiment, the additional pattern optimizer receives the one or more of the plurality of fields, the plurality of waveforms, the one or more spatio-temporal units, or the spatio-temporal pattern of neurostimulation that are approximately optimized by pattern optimizer and operates in an offline fashion to translate them to sets of stimulation parameters which may be programmed on a stimulating device, such as implantable stimulator 404, or additionally considers additional constraints, e.g., battery longevity. In another embodiment, the additional pattern optimizer operates in an online fashion to alter the stimulation parameters to suit the device, or to be suitable given additional constraints.

In various embodiments, external programming device 702 is implemented as multiple devices constituting a front end and a back end. In one embodiment, the front end and the back end are similar, and involve optionally first the creation and storage of sets of fields and patterns, and second the combination of fields and patterns for use in programming the device, or otherwise first the programming of fields and patterns directly onto the device, where in some embodiments filers/optimizers are acting online to limit or modulate programming, or suggest alterations in programming which may optionally be selected by the programmer. In one embodiment, the front end is on one device (e.g., a Clinician's Programmer (CP, a programming device configured for use by the user such as a clinician attending the patient in whom implantable system 422 is placed), a computer, or an application on a smartphone) and the back end is elsewhere (e.g., "the cloud", the user's computer/server, or the manufacturer's computer/server).

In one embodiment, the first act of creating fields and patterns can be done without a patient present, and optionally on a device other than a CP. For example, the fields and patterns may be created based on information collected and/or derived from a patient population and/or each individual patient. Such information may be used to develop and/or customize computational models representing portions of a patient's nervous system for evaluating responses to neurostimulation, such as one or more neuronal network models 750.

Table 1 shows an example of fields (spatial patterns) and waveforms (temporal patterns) stored in a library such as pattern library 748. Table 2 shows an example of fields and waveforms used to generate a spatio-temporal pattern of neurostimulation.

TABLE 1

| Fields | Waveforms |
|---|---|
| F1 | P1 |
| F2 | P2 |
| ... | ... |
| FN | PN |

TABLE 2

| Fields | Waveforms |
|---|---|
| F1 | P1 + P2 |
| F2 + F3 | P2 + P3, P1 |
| ... | ... |
| FN | PN |

In one embodiment, fields and patterns are combined in a programming device (also referred to as a "player"), such as external programming device 702, in a manner in which the patient must experience some complete set or representative set of stimulation before settings can be saved to stimulator. In one embodiment, this representative set of stimulation may not be identical to the full programmed settings, but may include highlights that are automatically chosen, optionally with input from the user. For example, in the case where two fields (F's) and patterns (waveforms, P's) are chosen where each pattern has a long run-time and they are run serially, the experiential program may be the first N seconds of field 1 (F1) pattern 1 (P1), following by the first N seconds of field 2 (F2) pattern 2 (P2). In one embodiment, the system may automatically generate a set of fields and patterns which are not identical to any whole fields and patterns or portions of fields and patterns created by the user, and this trial setting or set of settings can be used to determine that the proposed settings may be programmed.

In one embodiment, fields and patterns are entered into the player, and additional parameters are automatically used to adjust the stimulation. As an example, F1P1 and F2P2 are entered, but a desirable outcome involves the random alternation between F1P1 and F2P2, such that the player automatically sets programming settings related to, for example, the relative durations of F1P1 vs. F2P2.

In one embodiment, fields and patterns are entered into the player, and additional parameters are entered by the user to control the playing of the composition (i.e., controlling the delivery of neurostimulation according to the pattern of neurostimulation composed with the fields and patterns). In various embodiments, fields and patterns are entered into the player, and additional parameters are automatically generated by the player to control the playing of the composition. In various embodiments, the user can set general settings in the player, and such general settings are applied to all the field and pattern sets, for example upon being programmed in the patient for the first time (e.g., an initial stim amplitude ramp of 10 seconds).

In one embodiment, patterns can be programmed to play simultaneously (in combination) or serially (one at a time). For example, P1 may be a 40 Hz signal of square pulse shape of pulse width 20 µs, and P2 may be an 80 Hz signal with triangular pulse shape of pulse width 100 µs. The combination of P1 and P2 may be written as P1+P2 and result in both patterns playing simultaneously with some field or combination of fields, where P1 and P2 have a constant phase alignment. Alternatively, P1 and P2 may each have an associated duration, and play serially.

In one embodiment, patterns which can play simultaneously with all patterns without modification to any of the patterns are allowed, and patterns which would require e.g., arbitration are not allowed. In one embodiment, rows in Table 2 are played serially. In one embodiment, fields and patterns can be created as separate units, and combined for "playback". "Tracks" (rows in Table 2) can be set to repeat (e.g., continuously or for a specified number of repetitions), and sub-units of the track may be grouped for playing.

B. Neuronal Network Model

Figure 8:
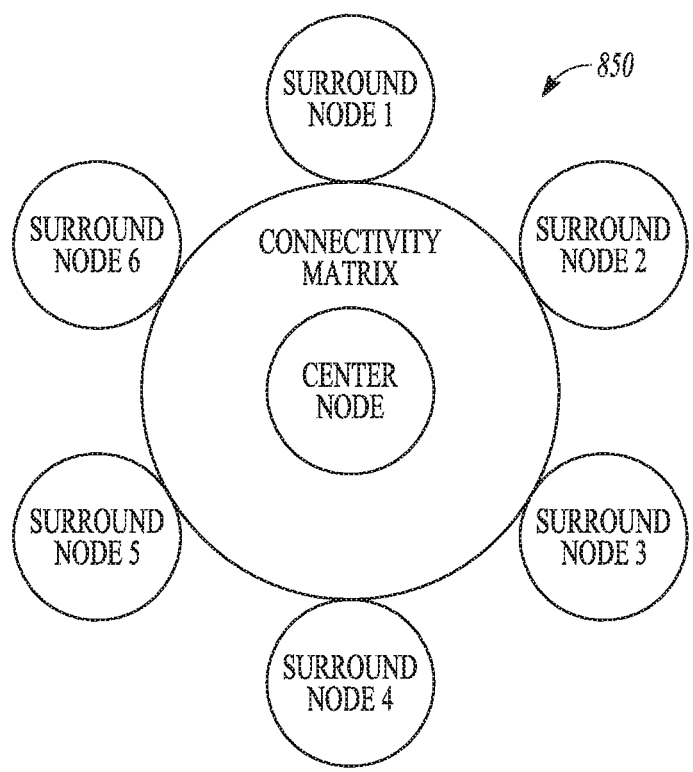
FIG. 8 illustrates an embodiment of a multi-nodal neuronal network model.

FIG. 8 illustrates an embodiment of a multi-nodal neuronal network model 850. Computational network models exist for various neuromodulation indications. These extant models, or new models, often represent simplified subunits of a functional whole. Each of these units may be replicated in order to form a multi-nodal model. This multi-nodal model may then be used to drive hypothesis generation, or be used in an "on-line" fashion, in some embodiments with live feedback and alteration of the model or its components, in order to improve programming of neurostimulation devices. In various embodiments, the one or more neuronal network models comprise at least one multi-nodal model including a plurality of nodes each representing a functional subunit of a nervous system. Such functional subunits may correspond to an anatomical subunit in the modeled portion of a nervous system or an abstraction that account for a function of the modeled portion of the nervous system. By way of example and not by way of limitation, neuronal network model 850 as illustrated in FIG. 8 includes a center node and six surround nodes 1-6. In various embodiments, neuronal network model 850 can include any number of interconnected nodes. Each of these nodes may represent a complete model or repetitions of a subset of the model. In various embodiments, neuronal network model 850, or any portion of neuronal network model 850, can be based on an existing model or an existing model augmented by one or more new components for a particular application (e.g., neurostimulation for a particular condition). The interconnections between these nodes may yield an overlapping repeating pattern of "receptive fields" and "surround fields" for each node in neuronal network model 850. This quality of the model may yield sensitivity to particular fields, patterns, or combinations of either or both. The connections between these nodes are represented as a connectivity matrix in FIG. 8. The strengths of various connections between nodes or elements of nodes may similarly be controlled, as well as the temporal delay between nodes or elements of nodes. In one embodiment, the importance given to any particular node of neuronal network model 850 during some evaluation may also be scaled by a weighting map. Node or elements of nodes may be differently weighted when calculating some output metric.

Multiple multi-nodal models such as neuronal network model 850 may be employed when evaluating some output metric such as, by way of example and not by way of limitation, a first multi-nodal model representing neural elements, and a second multi-nodal model representing supporting glial structures. These models may be functionally separated, output metrics from each may be calculated, and post-processing may take into account the results from each model when computing e.g., measures of success. Or, the models may functionally related, such that changes in one model propagate changes in the second. More than two models may be interconnected.

Figure 9:
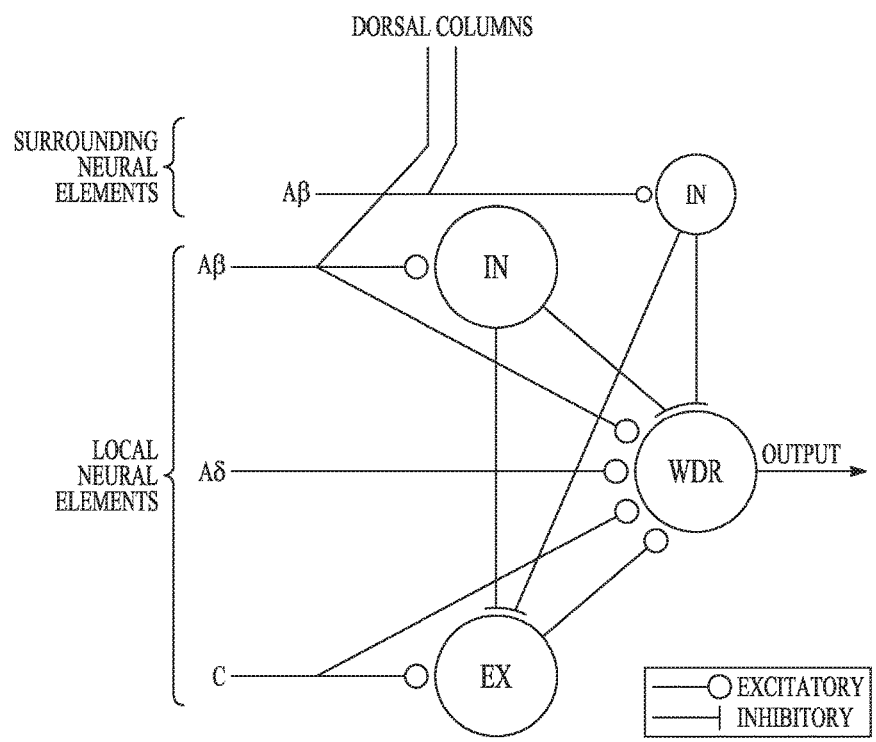
FIG. 9 illustrates an embodiment of a neuronal network model.
Figure 10:
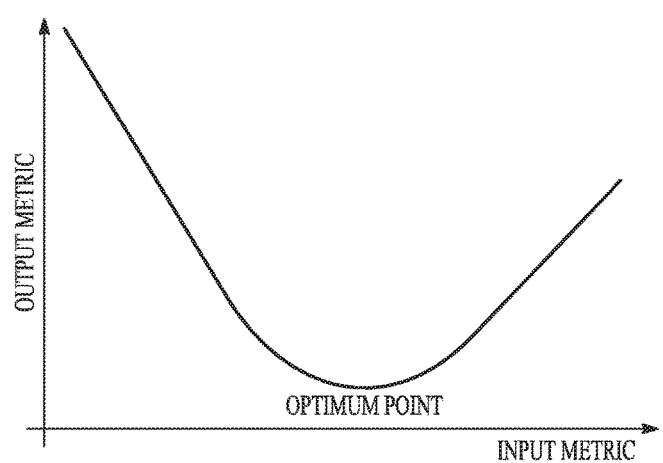
FIG. 10 illustrates characteristics of an exemplary simplified neuronal network model.

FIG. 9 illustrates an embodiment of a neuronal network model (hereinafter "Zhang Model"), which is discussed in T. C. Zhang, J. J. Janik, and W. M. Grill, "Modeling effects of spinal cord stimulation on wide-dynamic range dorsal horn neurons: influence of stimulation frequency and GABAergic inhibition", *J Neurophysiol* 112: 552-567, 2014. FIG. 10 illustrates an embodiment of the Zhang model that is a computational network model of the dorsal horn circuit. The model has a network architecture that is based on schemes of dorsal horn nociceptive processing, with biophysically based compartmental models of dorsal horn neurons connected via representations of excitatory and inhibitory synapses. As shown in FIG. 9. The model includes local neural elements (A$\beta$, A$\delta$, and C fibers), surrounding neural elements (different A$\beta$ fibers), inhibitory (IN) interneurons, an excitatory (EX) interneuron, and a wide-dynamic range (WDR) projection neuron in the dorsal horn. Parameters of the model can be determined and tuned using experimental data. Representation of SCS can be applied to the dorsal column input. In various embodiments, neuronal network model 850 can include multiple interconnected nodes, such as mutually inhibitory nodes. Each node can include a Zhang model such as the model illustrated in FIG. 9.

Alternately, each node consists of a model in which the neurons of the Zhang model are replaced by simpler models of neurons (e.g. the neurons are replaced by perfect or generalized integrate and fire neurons and the synapses are replaced by simple synaptic models, for example as discussed in Peter Dayan and L. F. Abbott, *Theoretical Neuroscience*, Chapter 7 (MIT Press 2001). The model parameters are fit so that the WDR neuron exhibits a U shaped turning curve: firing rate is lowest for a certain range of frequencies of inputs, as illustrated in FIG. 10. In various embodiments, the firing rate may represent the firing rate of a single neuron, an average firing rate for a plurality of neurons, a cumulative firing rate for a plurality of neurons, or a computed firing rate resulting from a mathematical or statistical operation. This alternative model is a substantial simplification of the Zhang model but may capture essential features of the Zhang model. A further simplification may involve considering each node as a generalized integrate and fire neuron with reciprocal inhibition to neighboring nodes, and the model parameters being fit to experimental data from WDR neurons as discussed in Wulfram Gerstner and Werner M. Kistler, *Spiking Neuron Models*, Chapter 4 (Cambridge University Press, 2002).

In various embodiments in which a multi-nodal neural network model is used, delivery of neurostimulation can be represented as an input delivered to a collection of nodes in a spatio-temporally specific manner. The output of the multi-nodal neural network model can indicate the effects of the delivery of neurostimulation, including therapeutic and/or side effect(s).

The inhibition of adjacent nodes can be tuned by measuring the perception threshold due to activation of one node and the percentage change in this threshold caused by activation of an adjacent node. However, it is also possible that the results found is robust to a wide range of choices of mutual inhibition, and tuning the mutual inhibition would be unnecessary.

In various embodiment, to optimize a spatio-temporal pattern of neurostimulation, a neuronal network model can be run with a wide range of spatio-temporal patterns and pulse shapes with the goal of minimizing the WDR output for specific groups of adjacent nodes over a wide dynamic range. The spatio-temporal pattern of neurostimulation that provide for an approximately minimum WDR output can be used to generate an initial set of the plurality of stimulation parameters controlling delivery of neurostimulation pulses from a stimulation device such as implantable stimulator 404.

In one embodiment, each node of a multi-nodal neural network model represents a paresthesia locus (or other loci, as discussed under "Paresthesia-Guided Field Selection" below). In this case, the model would consist of as many nodes as are necessary to capture the paresthesia loci and some additional nodes to capture the inhibitory effects of regions that may not directly be related to pain.

C. Neurostimulation for Cumulative Effects

In various embodiments, neurostimulation can be delivered to different fields, with different waveforms, and/or at different times for cumulative effects. For example, it may be desirable to enforce some stimulation effect while keeping certain stimulation thresholds (e.g., sub-paresthesia threshold) at each stimulation location.

In one embodiment, many repeated deliveries of neurostimulation along selected neural elements (e.g., a bundle of axon fibers) may imply repeated stimulations along the long axis of a lead in order to have many chances to result in an effect of the neurostimulation (e.g., an effect that depends on absolute timing to a signal which cannot be synced to). In one embodiment, a neuronal network model such as neuronal network model 850 is used to determine how repetitions of the neuro stimulation can be configured, for example, in space (e.g., not repeated within 5 mm, or 1.5 times the width of the volume of tissue activated) or in time (e.g., not repeated within 12 ms, or not within 2 synaptic delays and 4 ms of conduction delay).

In various embodiments, using a neuronal network model such as neuronal network model 850, a first set and a second set of programming parameters can be designed, where the application of neither set alone has the desired effect, but the application of both sets yields the desired effect. This concept can be extended to more than two sets of programming parameters which have a synergistic relationship. For example, the application of one set may result in a desired effect but with undesired side effects, and the application of the other set may abate the side effects. This occurs in a manner that can be more complex than, for example, simply using flanking anodes to shrink the activating field of some cathodes.

Figure 11:
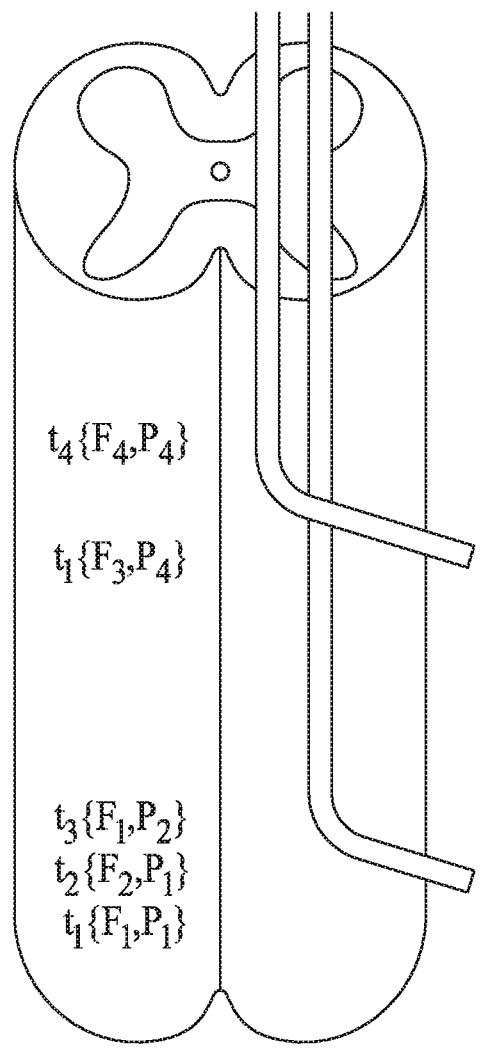
FIG. 11 illustrates an embodiment of neurostimulation for cumulative effects.

FIG. 11 illustrates an embodiment of neurostimulation for cumulative effects. In FIG. 11, stimulation times $t_N$ represent phase alignments (relative rather than absolute time). Cumulative stimulation regions may be close to each other or far apart from each other in space. These regions may target the same or similar neural elements at multiple locations, or may target related neural elements at various positions within their network. Stimulation regions may be tightly or more separated in space. In FIG. 11, the locations of $t_N(F_N, P_N)$ illustrate approximate field locations. In various embodiments, a neuronal network model such as neuronal network model 850 can be used to analyze the cumulative effects of neurostimulation applied according to $t_N(F_N, P_N)$. In various embodiments, a neuronal network model such as neuronal network model 850 can be used to determine an approximately optimal set of $t_N(F_N, P_N)$ for achieving specified desirable cumulative effects.

D. Robust Configuration for Neurostimulation

In various embodiments, optimization of stimulation configurations can include searching for stimulation configurations that are robust (meeting the objective to the greatest possible extent) under a range of changing conditions. Value and applicability of a stimulation configuration is greater for increasing number of conditions in which it performs well, even though under some of these conditions a different configuration may perform better. Such optimization of stimulation configurations is referred to as robust configuration for neurostimulation. In various embodiments, such robust configuration for neurostimulation can be performed using a neuronal network model such as neuronal network model 850.

In various embodiments, the robust configuration for neurostimulation can be applied to design a stimulation field shape which is robust to small changes in absolute or relative position, for example, with respect to a target or reference structure of interest (e.g., midline, vertebral level, large vessels, numbered or physiologically identified root) in the patient's body. Examples of such small changes include electrode displacement after implantation in the patient, physiological or anatomical changes in the patient over time, and physiological or anatomical variances among patients. In such examples, the robust configuration for neurostimulation can reduce the need for adjustment of settings for each patient over time and/or reduce the extent of customization for each patient.

In various embodiments, the robust configuration for neurostimulation can be applied to design a stimulation pattern that is robust to changes in absolute or relative temporal alignment with one or more signals such as evoked compound action potential (ECAP), firing of a particular neuron, and natural or pathological signal peak frequency. The absolute or relative temporal alignment refers to the action being early or late from a desired time by a fixed amount, e.g., 1 minute or 1 second. Relative alignment refers to some characteristic of the desired timing.

In various embodiments, concepts of machine learning and decision-making can be employed, e.g., fuzzy optimization, multi-objective optimizations, or robust optimization may be employed in the robust configuration for neurostimulation.

In various embodiments, limits can be placed on the deviation allowable between maximum effect found and robust effect sought. For example, a robust configuration for neurostimulation results in a pattern or field, which has a metric of score 'X', this method would only consider patterns or fields with score X·α, where 0<α<1.

E. Multi-Step Optimization

In various embodiments, analysis using a neuronal network model such as neuronal network model 850 may suggest that a particular combination of two stimulation fields is desirable, but the relative locations of these two fields may depend on an individual patient's anatomy and physiology. Under such circumstances, a first field and waveform combination may be optimized, and then the other field and waveform combinations can be optimized with respect to the first field and waveform while the first field and waveform combination is being applied to deliver neurostimulation. In various embodiments, the two fields can be specified by using a neuronal network model, such as neuronal network model 850, to be applied in combination for achieving a specified effect.

Figure 12:
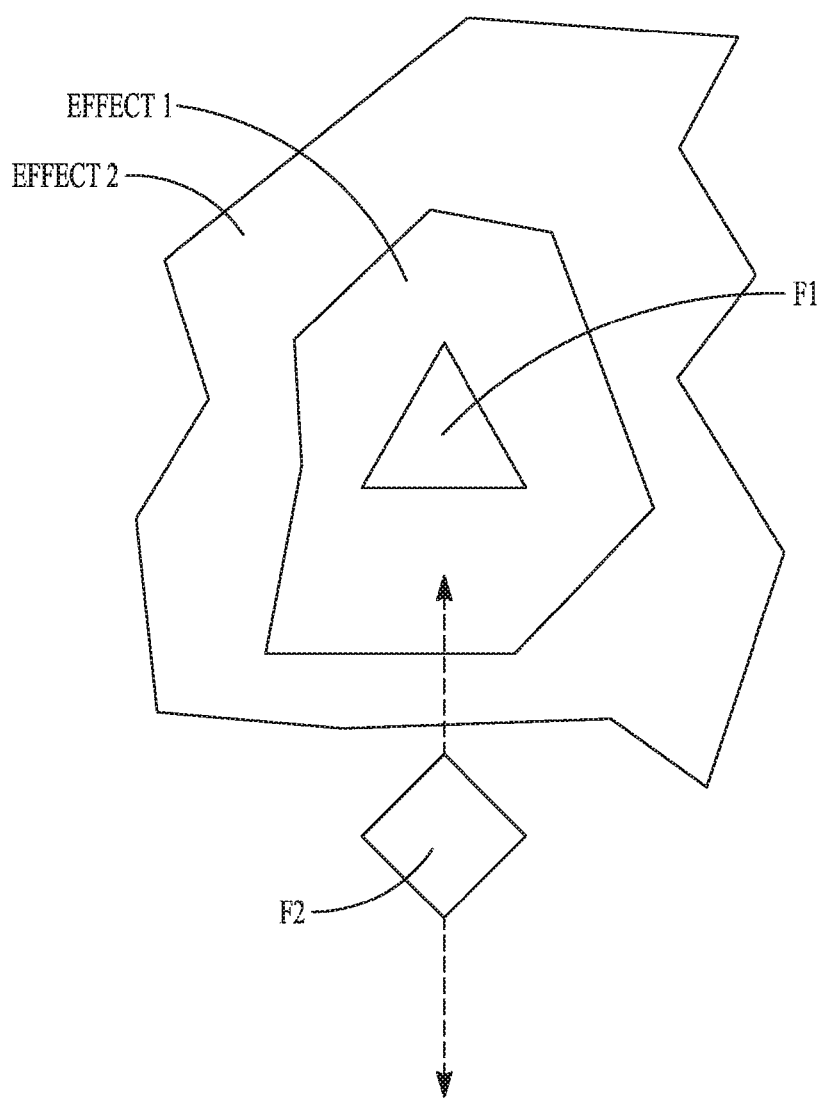
FIG. 12 illustrates an embodiment of multi-step optimization.

FIG. 12 illustrates an embodiment of multi-step optimization. As illustrated in FIG. 12, a first field (F1) and areas of effects of delivering neurostimulation through the first field (EFFECT 1, EFFECT2) are illustrated, and a second field (F2) is illustrated as being moved. The areas EFFECT 1 and EFFECT 2 each illustrate a region within which the response to the neurostimulation delivered through the first field is within a certain range, regardless of the position of the second field. These areas may be referred to as "false color map" when the areas are each coded in color. In various embodiments, areas EFFECT 1 and EFFECT 2 may each depict the intensity of a variable in a 2-dimensional plane. The first field may be placed according to one or more criteria, and then the second field may be placed with respect to the first field according to one or more criteria. In various embodiments, when the second field is optimized, the first field can be further optimized due to interaction with the second field. This can be repeated until the outcome is satisfactory.

F. Paresthesia-Guided Field Selection

In various embodiments, stimulation-induced sensations (such as paresthesia) can be used to guide spatial loci used for spatio-temporal methods. For example, sensation loci (such as paresthesia loci) can be identified and used as a starting point for identifying optimal fields for pain-control stimulation. In some cases, one or more locations of paresthesia created by neurostimulation correspond to regions of interest for applying the pain-control stimulation. Simulation with the Zhang Model (FIG. 9) for dual-frequency neurostimulation showed that multiple groups of neurons excited at distinct frequencies can reduce average WDR output (pain surrogate). While paresthesia is discussed as a specific example of stimulation-induced sensation, the present subject matter as applied using paresthesia loci can also be applied more generally to sensation loci. Thus, in the following discussions about paresthesia-guided field selection, "paresthesia" can be replaced with stimulation-induced sensation or a particular type of stimulation-induced sensation, and "paresthesia loci" can also be replaced by "sensation loci", which include spatial loci of the stimulation-induced sensation or the particular type of stimulation-induced sensation. In other words, the paresthesia-guided field selection as discussed in this document can be applied as sensation-guided field selection with the sensation being any stimulation-induced sensation or one or more particular types of stimulation-induced sensation.

With closed loop optimization of patterns of neurostimulation, the present system can help select the stimulation fields to be used. Many aspects of the present system can be applied as improvements to coordinated reset types of stimulation, since coordinated reset uses multiple field locations (but with a very specific temporal method).

Figure 13:
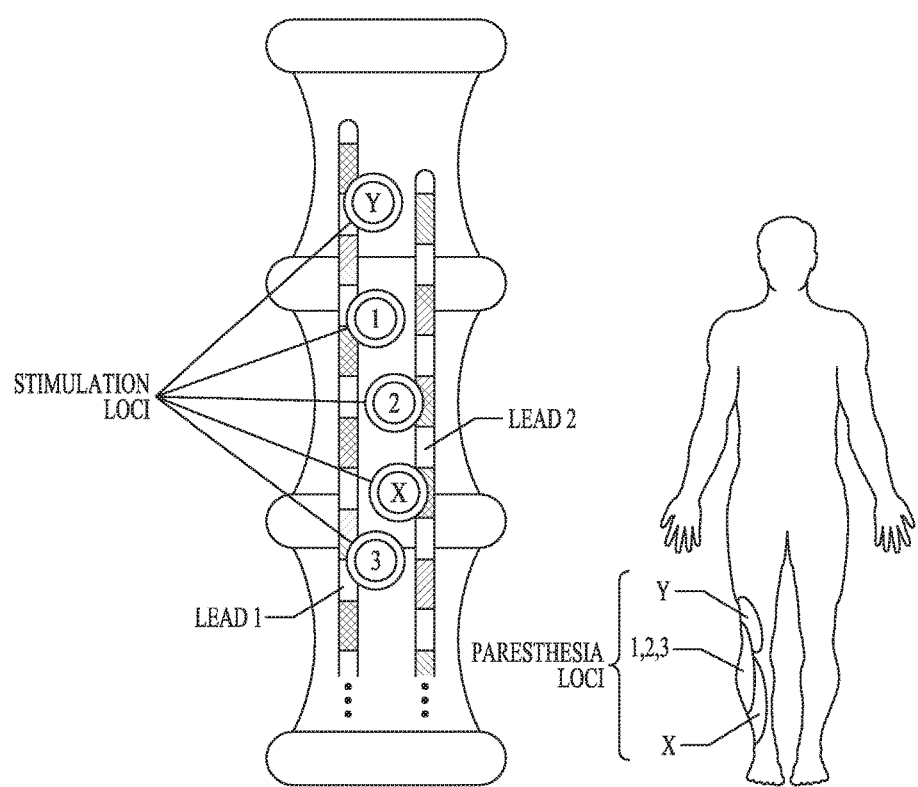
FIG. 13 illustrates an embodiment of identifying stimulation loci that generate paresthesia in a part of a body.

FIG. 13 illustrates an embodiment of identifying stimulation loci that generate paresthesia in a part of a body. FIG. 13 shows stimulation loci (1, 2, 3, X, and Y) associated with neurostimulation delivered through selected electrodes on two leads (LEAD 1 and LEAD 2), and their corresponding paresthesia loci. Current-steering and neural targeting programs (such as Illumina3D™ by Boston Scientific Neuromodulation Corporation) are able to identify multiple loci that generate paresthesia in a part of the body. It is possible that these stimulation loci correspond to distinct groups of "local" axons (although, even though the patient feels the paresthesia in a similar location, it is likely that there is surround inhibition connectivity). Therefore, the current-steering and neural targeting programs can be used to find groups of "local" neural elements for which spatio-temporal methods can be employed using a dual or multiple stimulation frequencies. Often, it is possible to find more than 2 loci, and it is likely that more than two groups would be able to improve over two groups. Candidate temporal patterns include: (1) dual-frequency mode stimulation (delivering neurostimulation with two different stimulation frequencies simultaneously to different fiber populations, e.g., T. C. Zhang, J. J. Janik, and W. M. Grill, "Modeling effects of spinal cord stimulation on wide-dynamic range dorsal horn neurons: influence of stimulation frequency and GABAergic inhibition", *J Neurophysiol* 112: 552-567, 2014), (2) patterns derived from a model for multiple groups of local and/or surround neural elements using computational optimization, (3) patterns derived from a model for multiple groups of local and/or surround neural elements using pre-clinical model optimization, (4) patterns derived from a model for multiple groups of local and/or surround neural elements using in-vivo optimization via e-diary feedback by patient or objective quantitative measures (e.g., activity, heart rate variability, etc.), and (5) stimulation patterns similar to coordinated reset type of stimulation (desynchronized neurostimulation based on temporally coordinated phase resets of sub-populations of a synchronized neuronal ensemble, e.g., P. A. Tass, Desynchronization by Means of a Coordinated Reset of Neural Sub-Populations, *Progress of Theoretical Physics Supplement*, No. 150, 281-296 (2003)).

It is possible to identify regions of stimulation that are neighboring with no or some (but not complete) overlap (e.g., X and Y in FIG. 13). Inclusion of these "surround" regions in the spatio-temporal method can be used. These regions may not be as sensitive as a pain region, but may be stimulated to participate in the surround inhibition effect.

Using current-steering and/or neural targeting programs with tight contact spacing can be a particularly good way to selectively stimulate dorsal roots or portions of a dorsal root. That is, by choosing stimulation loci that are lateral (near to each other in the neighborhood of the root), one may be able to select for stimulation multiple groups of neurons (perhaps overlapping) that pertain to a common part of the body and a common neural network.

In one embodiment, several root-based stimulation loci are selected for the spatio-temporal method. In one embodiment, both dorsal column and dorsal root-based loci are selected.

In one embodiment, in addition to multiple loci, multiple waveforms are used in the spatio-temporal method. These waveforms are designed to modulate different groups (possibly overlapping) of neural elements at different times (e.g., pre-pulse, long-duration pulse, with and without anodic intensification, etc.).

In one embodiment, stimulation of surround areas is preferred because it does not include WDR excitation in the painful region but does include inhibition. For example, stimulation in the surround region can be initiated, and then over time the stimulation reaches the painful region (i.e., the pain region is squeezed with stimulation over time).

Figure 14:
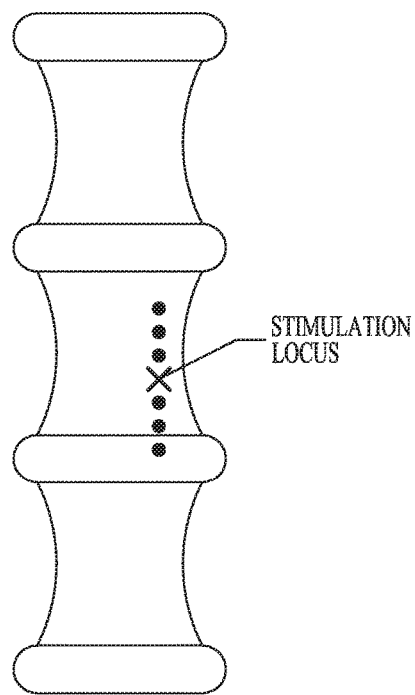
FIG. 14 illustrates an embodiment of a stimulation locus over roots identified via a paresthesia-based method.
Figure 15:
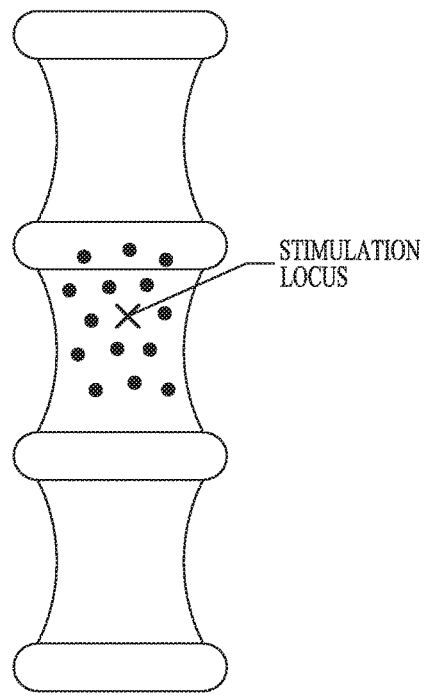
FIG. 15 illustrates another embodiment of a stimulation locus over roots identified via a paresthesia-based method.

FIGS. 14 and 15 each illustrate an embodiment of a stimulation locus over roots identified via a paresthesia-based method. In one embodiment, paresthesia is used to identify a locus in lead or anatomy space that corresponds to paresthesia at or surrounding the painful region, and based on that locus, a number of other loci are automatically selected. As illustrated in FIG. 14 for example, a symbol X represents a stimulation locus over the roots identified via a paresthesia-based method. Once X is selected as a good "starting point", the system can automatically select a number of other spatially related points (such as the points indicated by the dots above and below X. Inputs may be fed to the neuronal network model, e.g. the paresthesia map, or fluoroscopy images, or a selection made from a set of presets, then the system can run the model, or use information or simulations. As illustrated in FIG. 15 for another example, the symbol X represents a stimulation locus over the dorsal columns identified via a paresthesia-based method. Once X is selected as a good "starting point" the system can automatically select a number of other spatially related points (such as the points indicated by the dots around the symbol X). In some embodiments, the spatial arrangement of the additional points is pre-selected for the user. In another embodiment, the user can create or modify the arrangement of the additional points relative to the starting point or points. In one embodiment, the user has access to or can create a library of spatial arrangements (e.g., an arrangement for roots, an arrangement for columns, a tight arrangement (perhaps for focal pain), a broad arrangement (perhaps for complex diffuse pain), etc.).

G. Anatomy-Guided Field Selection

In various embodiments, anatomy is used to guide spatial loci used for spatio-temporal methods. Referring to FIGS. 14 and 15, anatomy-guided field selection is similar to the paresthesia-guided field selection as discussed above, except for that the "starting point" is based on patient anatomy, pain region, and lead positions. For example, for left foot pain, a specific anatomically-based point or set of points might be chosen as the starting point or center of a set of points. This method uses existing knowledge between anatomical relationship between the location of pain and sites for stimulation that may control the pain.

In one embodiment, the set of points is further selected based on the "lead or electrode coverage" of the region to be modulated. In one embodiment, the user identifies or "paints" the pain loci on a "paresthesia person" and the group of points for the spatio-temporal method is automatically chosen based on a look-up table. In one embodiment, the pain diagnosis is another dimension used to select the points and/or other stimulation parameter in the spatio-temporal method. In one embodiment, the pain region and diagnosis can be entered into a system prior to lead placement, and the system will show the user where lead or electrode coverage is desired.

H. Spatio-Temporal Filtering to Reduce Spatial Sensitivity

Figures 16, 17:
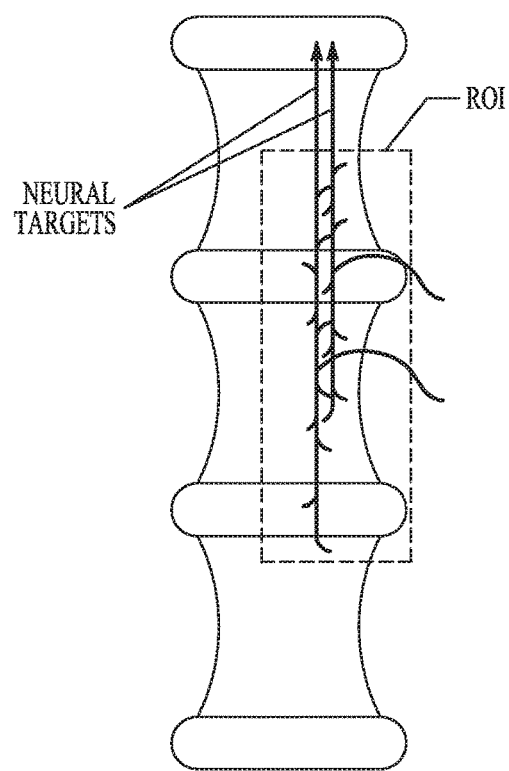
FIG. 16 illustrates an embodiment of a region of interest (ROI) for using spatio-temporal filtering to reduce spatial sensitivity.
FIG. 17 illustrates an embodiment of an ROI, such as the ROI of FIG. 16, divided into a plurality of sub-regions.

In various embodiments, spatio-temporal filtering within a region of interest (ROI) is applied to reduce sensitivity to the field in the patient's response to the neurostimulation. FIG. 16 illustrates an embodiment of an ROI for using spatio-temporal filtering to reduce spatial sensitivity. Success of neurostimulation may be contingent on delivering stimuli to exactly the right spot to engage exactly the right neural elements. When identifying and/or maintaining the exact location for such a "right spot" is difficult, an alternative is to use a filter to modulate the information that is generated or conveyed through a ROI that is less spatially specific than the "right spot."

FIG. 16 shows an example ROI that is chosen for filtering. A large amount of neural information is generated in or propagates through the ROI, and a "filter" that uses a spatio-temporal method can be used to predict the information that reaches the neural or neuronal targets after being modulated through the ROI, as further discussed below with reference to FIG. 18. Examples of neural elements in the ROI (the neural targets illustrated in FIG. 16) that convey or process "information" include dorsal roots, dorsal columns, pre-synaptic and post-synaptic dorsal horn, and dorso-lateral finniculus.

Various spatio-temporal patterns could be useful in various embodiments. In one embodiment, the ROI is divided into a number of sub-regions, and each of the sub-regions or groups of sub-regions are electrically modulated at different points in time. FIG. 17 illustrates an embodiment of an ROI, such as the ROI of FIG. 16, divided into a plurality of sub-regions. In FIG. 17, the numbers can represent electrodes on a paddle lead, which in turn should stimulate distinct, but overlapping sub-regions. The timing could be determined by pseudo-random generator, noise simulating process, Poisson process, a regular pattern as determined randomly or optimized, guided by heuristic rules, etc. One example of optimization to generate an order-of-modulation to the sub-regions might be to choose to maximize a space-time distance measure (e.g., SpaceTimeDist=$\Sigma_i'' \Sigma_j'' (r_{ij} + \Delta t_{ij})$ for n points, where $r_{ij}$ is a measure of distance between i and j, and delta-t is a measure of time between i and j, and the measures are weighted/normalized appropriately). In one embodiment, the user is able to choose properties of the filter. For example: the average time required to cycle through every point in the filter, the statistical characteristics of a stochastic, random, or noisy process. In one embodiment, pulse-width, and/or amplitude, and/or pulse-shape, are also dimensions through which there is pulse-to-pulse variability. In one embodiment, typical inter-pulse durations correspond to frequencies in the range of 10 Hz-100 Hz (similar to the dual frequency stimulation). In another embodiment, the inter-pulse durations correspond to frequencies in the range of in the range of 100 Hz to 100 kHz. In one embodiment, particularly long pulses greater than 1 ms are used and neural firing for different neural elements happens at different times during the pulse. In one embodiment, the pulse duration is at least 2 ms or even 5 ms. In one embodiment the shapes of the pulses also change on a pulse-to-pulse basis such that the recruitment characteristic changes on a pulse-to-pulse basic.

Figure 18:
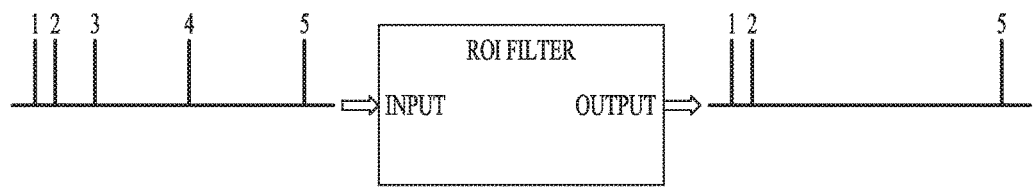
FIG. 18 illustrates an embodiment of a process using the spatio-temporal filtering to reduce spatial sensitivity.

FIG. 18 illustrates an embodiment of a process using the spatio-temporal filtering to reduce spatial sensitivity. The input to the ROI filter is the stimulation applied to a point in the ROI, the output of the ROI filter is the stimulation that would actually apply to a target spot in the neural targets, and the neuronal network model is used to produce the output given the input. The results of the process provides for a prediction of a region to which neurostimulation can be delivered to produce one or more specified effects.

Similar to the anatomy-guided field selection, in one embodiment, the ROI is automatically selected, for example, based on pain location, pain diagnosis, and/or lead location. In one embodiment, a plurality of spatially disparate ROIs can be used. In one embodiment, the number of sub-regions is a default number, such as 4. In another embodiment, the number of sub-regions can be changed by the user and can be up to tens of thousands. In one embodiment, the stimulation or modulation field for each sub-region is determined by an algorithm like the neural targeting program (e.g., Illumina3D™) for a given set of leads. In such an embodiment, the user may use target field shapes like tripoles or may select other shapes (e.g., monopoles, transverse fields, or other user-defined method). In one embodiment, the "modulation intensity" is kept within a specific range by using "normalized" values according to a strength-duration characteristic (to manage PW and Amplitude trade off) or according to another normalization approach (e.g., nonlinear model threshold evaluation).

ADDITIONAL EXAMPLES

In addition to those discussed in the SUMMARY section above, non-limiting examples of the present system are provided as follows:
(A. Neurostimulation Programming Using Neuronal Network Model)

In Example 1, a system for programming a neurostimulator to deliver neurostimulation pulses through a plurality of electrodes may include a storage device, a programming control circuit, and a pattern generator. The storage device may be configured to store a pattern library and one or more neuronal network models. The pattern library includes: a plurality of fields each specifying one or more electrodes selected from the plurality of electrodes and a spatial distribution of the selected one or more electrodes; and a plurality of waveforms each specifying a temporal pattern of a sequence of the neuromodulation pulses. The one or more neuronal network models are each a computational model configured to allow for evaluation of one or more fields selected from the plurality of fields in combination with one or more waveforms selected from the plurality of waveforms for one or more therapeutic effects in treating one or more indications for neuromodulation. The programming control circuit may be configured to generate a plurality of stimulation parameters controlling delivery of neurostimulation pulses from the neurostimulator according to a spatio-temporal pattern of neurostimulation specifying a sequence of neurostimulation pulses grouped as one or more spatio-temporal units each including one or more fields selected from the plurality of fields in combination with one or more waveforms selected from the plurality of waveforms. The pattern generator may be configured to generate the spatio-temporal pattern of neurostimulation and includes: a pattern editor configured to construct one or more of the plurality of fields, the plurality of waveforms, the one or more spatio-temporal units, or the spatio-temporal pattern of neurostimulation; and a pattern optimizer configured to approximately optimize one or more of the plurality of fields, the plurality of waveforms, the one or more spatio-temporal units, or the spatio-temporal pattern of neurostimulation using at least one neuronal network model of the one or more neuronal network models.

In Example 2, the subject matter of Example 1 may optionally be configured to include a first programmer configured to program the neurostimulator via a communication link and includes a programming output circuit to transmit the plurality of stimulation parameters to the neurostimulator, the programming control circuit coupled to the programming output circuit, and a user interface. The user interface includes a display screen, a user input device, and an interface control circuit coupled to the display screen and the user input device.

In Example 3, the subject matter of Example 2 may optionally be configured such that the first programmer further includes the storage device and the pattern generator, and wherein the interface control circuit includes the pattern generator.

In Example 4, the subject matter of Example 2 may optionally be configured to further include a second programmer configured to be communicatively coupled to the first programmer. The second programmer includes the storage device and the pattern generator. The user interface of the first programmer is configured to allow user-modification of the spatio-temporal pattern of neurostimulation generated by the pattern generator.

In Example 5, the subject matter of any one or any combination of Examples 1-4 may optionally be configured such that the one or more neuronal network models are configured to allow the pattern generator to generate an initial version of the spatio-temporal pattern of neurostimulation without presence of a patient.

In Example 6, the subject matter of any one or any combination of Examples 2-5 may optionally be configured such that the user interface is configured to allow testing of the spatio-temporal pattern of neurostimulation and to allow saving of only the tested spatio-temporal pattern of neurostimulation for use by the programming control circuit to generate the plurality of stimulation parameters.

In Example 7, the subject matter of Example 6 may optionally be configured such that the user interface is configured to allow testing of the spatio-temporal pattern of neurostimulation using a test pattern representative of the spatio-temporal pattern of neurostimulation.

In Example 8, the subject matter of Example 7 may optionally be configured such that the pattern generator is configured to generate the test pattern being a shortened version of the spatio-temporal pattern of neurostimulation that includes all of the one or more spatio-temporal units of the spatio-temporal pattern of neurostimulation.

In Example 9, the subject matter of Example 7 may optionally be configured such that the pattern generator is configured to generate the test pattern including various spatio-temporal units for determining the one or more spatio-temporal units used in the spatio-temporal pattern of neurostimulation.

In Example 10, the subject matter of any one or any combination of Examples 1-9 may optionally be configured such that the pattern generator is configured to automatically produce parameters for generating the spatio-temporal pattern of neurostimulation after the one or more spatio-temporal units are specified.

In Example 11, the subject matter of Example 10 may optionally be configured such that the pattern generator is configured to automatically produce the parameters including parameters controlling a duration of each spatio-temporal unit.

In Example 12, the subject matter of Example 10 may optionally be configured such that the pattern generator is configured to automatically produce the parameters including parameters controlling an order of the spatio-temporal units in the spatio-temporal pattern of neurostimulation when the one or more spatio-temporal units include a plurality of spatio-temporal units.

In Example 13, the subject matter of any one or any combination of Examples 1-12 may optionally be configured such that the interface control circuit is configured to allow user-specification of the one or more spatio-temporal units.

In Example 14, the subject matter of any one or any combination of Examples 1-13 may optionally be configured such that the one or more spatio-temporal units include a plurality of spatio-temporal units, and the pattern generator is configured to generate the spatio-temporal pattern of neurostimulation including two or more spatio-temporal units of the plurality of spatio-temporal units to be arranged concurrently or sequentially in time.

In Example 15, the subject matter of Example 14 may optionally be configured such that the pattern generator is configured to allow the two or more spatio-temporal units of the plurality of spatio-temporal units to be arranged concurrently in time upon checking specified rules of compatibility.

(B. Neuronal Network Model)

In Example 16, the subject matter of any one or any combination of Examples 1-15 may optionally be configured such that the one or more neuronal network models are each constructed for one of the one or more indications for neuromodulation.

In Example 17, the subject matter of any one or any combination of Examples 1-16 may optionally be configured such that the one or more neuronal network models include at least one multi-nodal model including a plurality of nodes each representing a functional subunit of a patient's nervous system.

In Example 18, the subject matter of Examples 17 may optionally be configured such that the multi-nodal model includes replicated nodes interconnected to form an overlapping repeating pattern of receptive fields and surround fields for each node of the replicated nodes.

In Example 19, the subject matter of Examples 18 may optionally be configured such that the interconnections between the replicated nodes have adjustable strengths.

In Example 20, the subject matter of any one or any combination of Examples 18 and 19 may optionally be configured such that the interconnections between the replicated nodes have adjustable temporal delays.

In Example 21, the subject matter of any one or any combination of Examples 17-20 may optionally be configured such that the multi-nodal model further includes a weighting map assigning weighting factors to each node of the plurality of notes for the evaluation of the one or more fields selected from the plurality of fields in combination with the one or more waveforms selected from the plurality of waveforms for therapeutic effects in treating the one or more indications for neuromodulation.

In Example 22, the subject matter of any one or any combination of Examples 17-21 may optionally be configured such that the one or more neuronal network models includes a plurality of multi-nodal models each representing a different functional or structural unit of the patient's nervous system.

In Example 23, the subject matter of any one or any combination of Examples 17-22 may optionally be configured such that the multi-nodal model includes mutually inhibitory nodes.

In Example 24, the subject matter of any one or any combination of Examples 17-22 may optionally be configured such that the multi-nodal model include nodes each including a neuron having a firing rate being lowest for a range of frequencies at which pulses of the neurostimulation pulses are delivered.

In Example 25, the subject matter of any one or any combination of Examples 17-24 may optionally be configured such that the multi-nodal model include inputs for the neurostimulation pulses to be delivered to a specified collection of nodes of the plurality of nodes in a spatially specific manner.

In Example 26, the subject matter of any one or any combination of Examples 17-25 may optionally be configured such that the multi-nodal model include adjacent nodes of the plurality of nodes with connections tuned by measuring a perception threshold due to activation of one node and a percentage change in that perception threshold caused by activation of an adjacent node.

In Example 27, the subject matter of any one or any combination of Examples 17-26 may optionally be configured such that the multi-nodal model include one or more nodes each corresponding to an electrode of the plurality of electrodes.

In Example 28, the subject matter of any one or any combination of Examples 17-26 may optionally be configured such that the multi-nodal model include one or more nodes each corresponding to a paresthesia locus and an output being a surrogate for pain.

In Example 29, the subject matter of any one or any combination of Examples 1-28 may optionally be configured such that the one or more neuronal network models are validated using experimental data.

In Example 30, the subject matter of any one or any combination of Examples 1-29 may optionally be configured such that the one or more neuronal network models each include inputs each associated with an electrode selected from the plurality of electrodes and an output representative of an indication of the one or more indications for neuromodulation.

(C. Neurostimulation for Cumulative Effects)

In Example 31, the subject matter of any one or any combination of Examples 1-30 may optionally be configured such that the spatio-temporal pattern of neurostimulation includes a series of sub-patterns constructed to treat an indication of the one or more indications for neuromodulation.

In Example 32, the subject matter of Example 31 may optionally be configured such that the pattern generator is configured to generate each sub-pattern of the series of sub-patterns such that pulses of the neurostimulation pulses delivered according to the spatio-temporal pattern of neurostimulation have a cumulative effect in treating the indication without causing one or more specified side effects.

In Example 33, the subject matter of Example 32 may optionally be configured such that the pattern generator is configured to generate each sub-pattern of the series of sub-patterns such that pulses of the neurostimulation pulses delivered according to the spatio-temporal pattern of neurostimulation have a cumulative effect in treating pain without causing paresthesia or without causing an intolerable level of paresthesia.

In Example 34, the subject matter of any one or any combination of Examples 31-33 may optionally be configured such that the pattern optimizer is configured to optimize each sub-pattern of the series of sub-pattern individually using the at least one neuronal network model.

In Example 35, the subject matter of any one or any combination of Examples 31-34 may optionally be configured such that the one or more neuronal network models include at least one model including inputs corresponding to one or more fields of the plurality of field specified in the series of sub-patterns and outputs each representing an effect in treating an indication of the one or more indication for neuromodulation or a side effect.

In Example 36, the subject matter of any one or any combination of Examples 31-35 may optionally be configured such that the series of sub-patterns includes a first sub-pattern constructed to have a therapeutic effect in treating the indication of the one or more indications for neuromodulation, and an additional sub-pattern.

In Example 37, the subject matter of Example 36 may optionally be configured such that the additional sub-pattern is constructed to enhance the therapeutic effect.

In Example 38, the subject matter of any one or any combination of Examples 36 and 37 may optionally be configured such that the first sub-pattern is associated with a side effect, and the additional sub-pattern is constructed to abate the side effect.

In Example 39, the subject matter of any one or any combination of Examples 36-38 may optionally be configured such that the first and second sub-patterns include identical fields selected from the plurality of fields.

In Example 40, the subject matter of any one or any combination of Examples 36-38 may optionally be configured such that the first and second sub-patterns include different fields selected from the plurality of fields.

(D. Robust Configuration for Neurostimulation)

In Example 41, the subject matter of any one or any combination of Examples 1-30 may optionally be configured such that the one or more neuronal network models include at least one robust model configured to allow for evaluation of one or more fields selected from the plurality of fields in combination with one or more waveforms selected from the plurality of waveforms for at least one therapeutic effect of the one or more therapeutic effects under a specified range of conditions.

In Example 42, the subject matter of Example 41 may optionally be configured such that the pattern optimizer is configured to approximately optimize the spatio-temporal pattern of neurostimulation for the at least one therapeutic effect under the specified range of conditions using the at least one robust model.

In Example 43, the subject matter of Example 41 may optionally be configured such that the pattern optimizer is configured to approximately optimize the spatio-temporal pattern of neurostimulation for the at least one therapeutic effect under a maximum range of conditions within the specified range of conditions using the at least one robust model.

In Example 44, the subject matter of any one or any combination of Examples 41-43 may optionally be configured such that the pattern optimizer is configured to approximately optimize the one or more fields selected for the spatio-temporal pattern of neurostimulation using the at least one robust model for minimizing changes in the at least one therapeutic effect due to a change in the position of each of the one or more fields relative to a reference structure in the patient.

In Example 45, the subject matter of Example 44 may optionally be configured such that the reference structure includes a midline, a vertebral level, a large vessel, or a numbered or physiologically identified root, or relative position given another structural or functional landmark.

In Example 46, the subject matter of any one or any combination of Examples 41-45 may optionally be configured such that the pattern optimizer is configured to approximately optimize the spatio-temporal pattern of neurostimulation using the at least one robust model for minimizing changes in the at least one therapeutic effect due to a change in a physiological signal sensed from the patient or a change in a signal computed from the physiological signal.

In Example 47, the subject matter of Example 46 may optionally be configured such that the change in the physiological signal includes a change in an evoked compound action potential (ECAP), a change in firing of a particular neuron or a particular group of neurons, a change in a peak frequency of the physiological signal.

In Example 48, the subject matter of any one or any combination of Examples 41-47 may optionally be configured such that the one or more neuronal network models includes at least one model configured to allow for the evaluation of the one or more fields selected from the plurality of fields in combination with the one or more waveforms selected from the plurality of waveforms for the one or more therapeutic effects using machine learning and decision making.

In Example 49, the subject matter of Example 48 may optionally be configured such that the one or more neuronal network models includes at least one model configured to allow for a fuzzy optimization, a multi-objective optimizations, or a robust optimization of the spatio-temporal pattern of neurostimulation.

(E. Multi-Step Optimization)

In Example 50, the subject matter of any one or any combination of Examples 1-30 may optionally be configured such that the pattern optimizer is configured to approximately optimize the spatio-temporal pattern of neurostimulation in a plurality of optimization steps using the at least one neuronal network model.

In Example 51, the subject matter of Example 50 may optionally be configured such that the spatio-temporal pattern of neurostimulation specifies a sequence of neurostimulation pulses grouped as at least a first spatio-temporal unit and a second spatio-temporal unit of the one or more spatio-temporal units, and the pattern optimizer is configured to approximately optimize the first spatio-temporal unit in a first optimization step of the plurality of optimization steps and approximately optimize the second spatio-temporal unit in a second optimization step of the plurality of optimization steps.

In Example 52, the subject matter of Example 51 may optionally be configured such that the pattern optimizer is configured to approximately optimize the second spatio-temporal unit with respect to the first spatio-temporal unit in the second optimization step.

In Example 53, the subject matter of any one or any combination of Examples 50 and 51 may optionally be configured such that the pattern optimizer is configured to approximately optimize the first spatio-temporal unit and the second spatio-temporal unit for a common therapeutic effect of the one or more therapeutic effects.

(F. Paresthesia-Guided Field Selection)

In Example 54, the subject matter of any one or any combination of Examples 1-53 may optionally be configured such that the one or more neuronal network models include a pain model configured to allow optimization of the spatio-temporal pattern of neurostimulation using paresthesia as guide.

In Example 55, the subject matter of Examples 54 may optionally be configured such that the pattern optimizer is configured to approximately optimize the spatio-temporal pattern of neurostimulation using the pain model and one or more known paresthesia loci each being a set of fields of the plurality of fields identified for causing paresthesia.

In Example 56, the subject matter of Example 55 may optionally be configured such that the pattern optimizer is configured to approximately optimize the spatio-temporal pattern of neurostimulation using the pain model and at least two known paresthesia loci.

In Example 57, the subject matter of any one or any combination of Examples 55 and 56 may optionally be configured such that the pattern optimizer is configured to approximately optimize the spatio-temporal pattern of neurostimulation by using the one or more known paresthesia loci as fields selected from the plurality of fields and approximately optimizing a waveform associated with each of the selected fields.

In Example 58, the subject matter of any one or any combination of Examples 55-57 may optionally be configured such that the pattern optimizer is configured to approximately optimize the spatio-temporal pattern of neurostimulation by using one or more regions surrounding the one or more known paresthesia loci as fields selected from the plurality of fields and approximately optimizing a waveform associated with each of the selected fields.

In Example 59, the subject matter of Example 58 may optionally be configured such that the pattern optimizer is configured to optimize one or more pulse frequencies of the waveform associated with each of the selected fields.

In Example 60, the subject matter of Example 58 may optionally be configured such that the pattern optimizer is configured to approximately optimize the spatio-temporal pattern of neurostimulation by using the one or more known paresthesia loci and one or more regions surrounding the one or more known paresthesia loci as fields selected from the plurality of fields and approximately optimizing a waveform associated with each of the selected fields.

In Example 61, the subject matter of any one or any combination of Examples 54-60 may optionally be configured such that the pain model is validated using pre-clinical data.

In Example 62, the subject matter of any one or any combination of Examples 54-61 may optionally be configured such that the pain model is validated using clinical data collection from a patient population.

In Example 63, the subject matter of any one or any combination of Examples 54-62 may optionally be configured such that the pain model is validated using data collected from an individual patient.

In Example 64, the subject matter of any one or any combination of Examples 54-63 may optionally be configured such that the pattern optimizer is configured to approximately optimize the spatio-temporal pattern of neurostimulation using dorsal root fields selected from the plurality of fields as the one or more fields specified in the spatio-temporal pattern of neurostimulation, the dorsal root fields each specifying one or more electrodes selected from the plurality of electrodes to be placed in one or more dorsal roots.

In Example 65, the subject matter of any one or any combination of Examples 54-64 may optionally be configured such that the pattern optimizer is configured to approximately optimize the spatio-temporal pattern of neurostimulation using dorsal column fields selected from the plurality of fields as the one or more fields specified in the spatio-temporal pattern of neurostimulation. The dorsal column fields each specify one or more electrodes selected from the plurality of electrodes to be placed in one or more dorsal columns.

In Example 66, the subject matter of any one or any combination of Examples 54-65 may optionally be configured such that the pattern optimizer is configured to approximately optimize the spatio-temporal pattern of neurostimulation using a plurality of different waveforms selected from the plurality of waveforms as the one or more waveforms specified in the spatio-temporal pattern of neurostimulation.

In Example 67, the subject matter of Example 66 may optionally be configured such that the pattern optimizer is configured to approximately optimize the spatio-temporal pattern of neurostimulation by including different spatio-temporal units of the one or more spatio-temporal units, the different spatio-temporal units targeting different regions of the patient's nervous system for delivering pulses of the neurostimulation pulses at times individually specified for each region of the different regions.

In Example 68, the subject matter of any one or any combination of Examples 57-67 may optionally be configured such that the pattern optimizer is configured to approximately optimize the spatio-temporal pattern of neurostimulation by using the pain model and anatomy of regions of the one or more known paresthesia loci to identify additional one or more fields selected from the plurality of fields and approximately optimizing a waveform associated with each of the selected one or more additional fields.

In Example 69, the subject matter of any one or any combination of Examples 57-68 may optionally be configured such that the user interface is configured to allow for user-modification of the fields selected by the pattern optimizer.

(G. Anatomy-Guided Field Selection)

In Example 70, the subject matter of any one or any combination of Examples 1-53 may optionally be configured such that the one or more neuronal network models include a pain model configured to allow optimization of the spatio-temporal pattern of neurostimulation using one or more locations of pain and one or more target regions to which neuromodulation is known to suppress the pain as a guide.

In Example 71, the subject matter of any one or any combination of Examples 1-53 may optionally be configured such that the pattern optimizer is configured to select one or more fields selected from the plurality of fields for use in the spatio-temporal pattern of neurostimulation based on the one or more locations of pain and one or more target regions.

In Example 72, the subject matter of any one or any combination of Examples 70 and 71 may optionally be configured such that the pattern optimizer is configured to identify one or more field for use in the spatio-temporal pattern of neurostimulation based on the one or more locations of pain and one or more target regions and add the identified one or more fields to the plurality of fields if the identified one or more fields are not already included in the plurality of fields.

In Example 73, the subject matter of any one or any combination of Examples 70-72 may optionally be configured such that the pattern optimizer includes a look-up table relating the one or more locations of pain to the one or more target regions, and identify the one or more target regions using a pain loci and the look-up table.

In Example 74, the subject matter of any one or any combination of Examples 70-73 may optionally be configured such that the pain model is further configured to allow optimization of the spatio-temporal pattern of neurostimulation using pain diagnosis as inputs.

In Example 75, the subject matter of any one or any combination of Examples 71-74 may optionally be configured such that the pattern optimizer is configured to generate a guide for placing the plurality of electrode in the patient based on the one or more fields specified in the spatio-temporal pattern of neurostimulation.

(H. Spatio-Temporal Filtering to Reduce Spatial Sensitivity)

In Example 76, the subject matter of any one or any combination of Examples 1-53 may optionally be configured such that the one or more neuronal network models include a region of interest (ROI) model representing a specified ROI including a neuronal target and divided into a plurality of sub-regions. The ROI model includes a target unit representing the neuronal target and a plurality of surround units each representing the plurality of sub-regions.

In Example 77, the subject matter of Example 76 may optionally be configured such that the ROI model is configured to represent a filter having inputs to receive pulses of the neurostimulation pulses received in one or more sub-regions of the plurality of sub-regions and an output representing the pulses as received by the neuronal target.

In Example 78, the subject matter of any one or any combination of Examples 76 and 77 may optionally be configured such that the neuronal target includes one or more neurons of the dorsal roots, dorsal columns, pre-synaptic dorsal horn, post-synaptic dorsal horn, or dorso-lateral finniculus.

In Example 79, the subject matter of any one or any combination of Examples 76-78 may optionally be configured such that the ROI model is configured to allow for evaluation of the one or more fields selected from the plurality of fields in combination with the one or more waveforms selected from the plurality of waveforms for one or more therapeutic effects in treating pain.

In Example 80, the subject matter of any one or any combination of Examples 76-79 may optionally be configured such that the pattern optimizer is configured to optimize the spatio-temporal pattern of neurostimulation using the ROI model, and the one or more fields in the spatio-temporal pattern of neurostimulation includes a plurality of ROI fields each specify a spatial distribution of the selected one or more electrodes within the ROI.

In Example 81, the subject matter of Example 80 may optionally be configured such that the ROI fields each correspond to one or more sub-regions of the plurality of sub-regions.

In Example 82, the subject matter of Example 81 may optionally be configured such that the one or more spatio-temporal units of the spatio-temporal pattern of neurostimulation include a plurality of ROI spatio-temporal units each including a field of the plurality of ROI fields in combination with one or more ROI waveforms selected from the plurality of waveforms, the pattern editor is configured to create the plurality of ROI fields, the one or more ROI waveforms, the plurality of ROI spatio-temporal units, and the spatio-temporal pattern of neurostimulation, and the pattern optimizer is configured to evaluate the spatio-temporal pattern of neurostimulation.

In Example 83, the subject matter of Example 82 may optionally be configured such that the pattern editor is configured to determine an order of the ROI spatio-temporal units in the spatio-temporal pattern of neurostimulation using a pseudo-random generator, a noise simulating process, a Poisson process, a random pattern, an optimized pattern, or one or more heuristic rules.

In Example 84, the subject matter of Example 82 may optionally be configured such that the pattern editor is configured to determine an order of the ROI spatio-temporal units in the spatio-temporal pattern of neurostimulation to maximize a space-time distance measure.

In Example 85, the subject matter of any one or any combination of Examples 82-84 may optionally be configured such that the pattern editor is configured to allow user adjustment of the plurality of ROI fields, the one or more ROI waveforms, the plurality of ROI spatio-temporal units, and the spatio-temporal pattern of neurostimulation.

In Example 86, the subject matter of any one or any combination of Examples 82-85 may optionally be configured such that the pattern editor is configured to create and adjust one or more of pulse amplitude, pulse width, or pulse shape of each pulse of the neurostimulation pulses.

In Example 87, the subject matter of any one or any combination of Examples 76-86 may optionally be configured such that the pattern editor is configured to specify the ROI based on a diagnosis identifying the neuronal target.

In Example 88, the subject matter of Example 87 may optionally be configured such that the pattern editor is configured to specify the ROI based on the diagnosis identifying the neuronal target and locations of the plurality of electrodes.

In Example 89, the subject matter of any one or any combination of Examples 87 and 88 may optionally be configured such that the pattern editor is configured to allow user specification of a number of sub-regions for the plurality of sub-regions of the ROI.

In Example 90, the subject matter of any one or any combination of Examples 87-90 may optionally be configured such that the pattern editor is configured to specify a plurality of spatially disparate ROIs.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation energy through a plurality of electrodes, the system comprising:
 a storage device configured to store:
  a pattern library including:
   a plurality of fields each specifying a spatial distribution of the neurostimulation energy across the plurality of electrodes; and
   a plurality of waveforms each specifying a temporal pattern of the neuromodulation energy; and
  one or more neuronal network models each being a computational model configured to allow for evaluating effects of one or more fields selected from the plurality of fields in combination with one or more waveforms selected from the plurality of waveforms in treating one or more indications for neuromodulation, the one or more neuronal network models including at least one or more of a first pain model or a second pain model, the first pain model configured to allow for optimization of the spatio-temporal pattern of neurostimulation using paresthesia as a first guide, the second pain model configured to allow for optimization of the spatio-temporal pattern of neurostimulation using one or more locations of pain and one or more target regions to which neuromodulation is known to suppress the pain as a second guide;
 a pattern generator configured to generate a spatio-temporal pattern of neurostimulation specifying a sequence of one or more spatio-temporal units each including one or more fields selected from the plurality of fields in combination with one or more waveforms selected from the plurality of waveforms, the pattern generator including:

a pattern editor configured to construct one or more of the plurality of fields, the plurality of waveforms, the one or more spatio-temporal units, or the spatio-temporal pattern of neurostimulation; and a pattern optimizer configured to optimize one or more of the plurality of fields, the plurality of waveforms, the one or more spatio-temporal units, or the spatio-temporal pattern of neurostimulation using at least one or more of the first pain model or the second pain model; and a neurostimulator configured to deliver the neurostimulation energy using the generated spatio-temporal pattern of neurostimulation.

2. The system of claim 1, wherein the one or more neuronal network models comprise the first pain model, and the pattern optimizer is configured to optimize the spatio-temporal pattern of neurostimulation using the first pain model and one or more known paresthesia loci each being a set of fields of the plurality of fields identified for causing paresthesia.

3. The system of claim 2, wherein the pattern optimizer is configured to optimize the spatio-temporal pattern of neurostimulation using the first pain model and at least two known paresthesia loci.

4. The system of claim 3, wherein the pattern optimizer is configured to optimize the spatio-temporal pattern of neurostimulation by using the one or more known paresthesia loci as fields selected from the plurality of fields and optimizing a waveform associated with each of the selected fields.

5. The system of claim 4, wherein the pattern optimizer is configured to optimize the spatio-temporal pattern of neurostimulation by using one or more regions surrounding the one or more known paresthesia loci as fields selected from the plurality of fields and optimizing a waveform associated with each of the selected fields.

6. The system of claim 5, wherein the pattern optimizer is configured to optimize one or more parameters of the waveform associated with each of the selected fields.

7. The system of claim 5, wherein the pattern optimizer is configured to optimize the spatio-temporal pattern of neurostimulation by using the one or more known paresthesia loci and one or more regions surrounding the one or more known paresthesia loci as fields selected from the plurality of fields and optimizing a waveform associated with each of the selected fields.

8. The system of claim 2, wherein the pattern optimizer is configured to optimize the spatio-temporal pattern of neurostimulation using a plurality of different waveforms selected from the plurality of waveforms as the one or more waveforms specified in the spatio-temporal pattern of neurostimulation.

9. The system of claim 8, wherein the pattern optimizer is configured to optimize the spatio-temporal pattern of neurostimulation by including different spatio-temporal units of the one or more spatio-temporal units, the different spatio-temporal units targeting different regions of the patient's nervous system for delivering portions of the neurostimulation energy at times individually specified for each region of the different regions.

10. The system of claim 9, wherein the pattern optimizer is configured to optimize the spatio-temporal pattern of neurostimulation by using the first pain model and anatomy of regions of the one or more known paresthesia loci to identify additional one or more fields selected from the plurality of fields and optimizing a waveform associated with each of the selected one or more additional fields.

11. The system of claim 1, wherein the one or more neuronal network models comprise the second pain model, and the pattern optimizer is configured to select one or more fields selected from the plurality of fields for use in the spatio-temporal pattern of neurostimulation based on the one or more locations of pain and one or more target regions.

12. The system of claim 11, wherein the pattern optimizer is configured to identify one or more field for use in the spatio-temporal pattern of neurostimulation based on the one or more locations of pain and one or more target regions and add the identified one or more fields to the plurality of fields if the identified one or more fields are not already included in the plurality of fields.

13. The system of claim 12, wherein the pattern optimizer comprises a look-up table relating the one or more locations of pain to the one or more target regions, and identify the one or more target regions using a pain loci and the look-up table.

14. The system of claim 13, wherein the second pain model is further configured to allow optimization of the spatio-temporal pattern of neurostimulation using pain diagnosis as inputs.

15. The system of claim 1, wherein the pattern optimizer is configured to generate a guide for placing the plurality of electrode based on the one or more fields specified in the spatio-temporal pattern of neurostimulation.

16. A method for delivering a neurostimulation energy using a neurostimulator, the method comprising:
providing a pattern library including:
a plurality of fields each specifying a spatial distribution of the neurostimulation energy across the plurality of electrodes; and
a plurality of waveforms each specifying a temporal pattern of the neuromodulation energy;
providing one or more neuronal network models each being a computational model configured to allow for evaluating effects of one or more fields selected from the plurality of fields in combination with one or more waveforms selected from the plurality of waveforms in treating one or more indications for neuromodulation, the one or more neuronal network models including at least one or more of a first pain model or a second pain model, the first pain model configured to allow for optimization of the spatio-temporal pattern of neurostimulation using paresthesia as a first guide, the second pain model configured to allow for optimization of the spatio-temporal pattern of neurostimulation using one or more locations of pain and one or more target regions to which neuromodulation is known to suppress the pain as a second guide;
generating a spatio-temporal pattern of neurostimulation specifying a sequence of one or more spatio-temporal units each including one or more fields selected from the plurality of fields in combination with one or more waveforms selected from the plurality of waveforms; and
delivering the neurostimulation energy from the neurostimulator using the generated spatio-temporal pattern of neurostimulation,
wherein generating the spatio-temporal pattern of neurostimulation includes:
constructing one or more of the plurality of fields, the plurality of waveforms, the one or more spatio-temporal units, or the spatio-temporal pattern of neurostimulation; and
optimizing one or more of the plurality of fields, the plurality of waveforms, the one or more spatio-temporal units, or the spatio-temporal pattern of neurostimulation using at least the one or more of the first pain model or the second pain model.

17. The method of claim 16, wherein providing the one or more neuronal network models comprises providing the first pain model, and optimizing the one or more of the plurality of fields, the plurality of waveforms, the one or more spatio-temporal units, or the spatio-temporal pattern of neurostimulation comprises optimizing the spatio-temporal pattern of neurostimulation using the first pain model and one or more known paresthesia loci each being a set of fields of the plurality of fields identified for causing paresthesia.

18. The method of claim 17, wherein optimizing the spatio-temporal pattern of neurostimulation comprises optimizing the spatio-temporal pattern of neurostimulation using a plurality of different waveforms selected from the plurality of waveforms as the one or more waveforms specified in the spatio-temporal pattern of neurostimulation.

19. The method of claim 16, wherein providing the one or more neuronal network models comprises providing the second pain model, and optimizing the one or more of the plurality of fields, the plurality of waveforms, the one or more spatio-temporal units, or the spatio-temporal pattern of neurostimulation comprises selecting one or more fields selected from the plurality of fields for use in the spatio-temporal pattern of neurostimulation based on the one or more locations of pain and one or more target regions.

20. The method of claim 16, further comprising generating a guide for placing the plurality of electrode based on the one or more fields specified in the spatio-temporal pattern of neurostimulation.

* * * * *